United States Patent
Kong et al.

(10) Patent No.: US 8,109,874 B2
(45) Date of Patent: Feb. 7, 2012

(54) MOBILE DEVICE HAVING HEALTH CARE FUNCTION BASED ON BIOMEDICAL SIGNALS AND HEALTH CARE METHOD USING THE SAME

(75) Inventors: Donggeon Kong, Busan (KR); Seokwon Bang, Kangnam-gu (KR); Hyoungki Lee, Kyungki-do (KR); Kyunghwan Kim, Kyungki-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1250 days.

(21) Appl. No.: 10/681,137

(22) Filed: Oct. 9, 2003

(65) Prior Publication Data

US 2004/0117212 A1 Jun. 17, 2004

(30) Foreign Application Priority Data

Oct. 9, 2002 (KR) .................. 10-2002-0061582

(51) Int. Cl.
*A61B 5/00* (2006.01)
(52) U.S. Cl. ........................ 600/300; 128/920
(58) Field of Classification Search .................. 600/300, 600/301; 128/903–905, 920
See application file for complete search history.

(56) References Cited

U.S. PATENT DOCUMENTS

| | | | |
|---|---|---|---|
| 2,339,579 A | 2/1941 | Milne et al. | |
| 5,601,090 A * | 2/1997 | Musha | 600/544 |
| 5,676,138 A * | 10/1997 | Zawilinski | 600/301 |
| 6,190,314 B1 * | 2/2001 | Ark et al. | 600/300 |
| 6,450,955 B1 | 9/2002 | Brown et al. | |
| 6,616,613 B1 * | 9/2003 | Goodman | 600/504 |

(Continued)

FOREIGN PATENT DOCUMENTS

EP    1 027 860 A1    8/2000

(Continued)

OTHER PUBLICATIONS

Takanobu Nagata et al., "Assessment of Autonomic Function and Mental Condition on Cardio-Respiratory Variability and Thermal Regulation by Using Neural Network", Proceedings of the 20th Annual International Conference of the IEEE Engineering in Medicine and Biology Society, 1998, pp. 364-366, vol. 20, No. 1, Hong Kong, China.

(Continued)

*Primary Examiner* — Henry M Johnson, III
*Assistant Examiner* — Kai Rajan
(74) *Attorney, Agent, or Firm* — Staas & Halsey LLP

(57) ABSTRACT

The present invention relates to a mobile device capable of performing biomedical signal measurement and a health care method using the same. It is an object of the present invention to provide a mobile device capable of efficiently performing health care functions for a user by checking a user's state of health using a handheld mobile device mounted with a biomedical signal measurement module, which can be used both as a mobile device and in measuring the emotional state and physical condition of a user if necessary, and a health care method using the same. In order to achieve the above object, the mobile device of the present invention comprises a biomedical signal measurement module for detecting biomedical signals from a user's body, classifying the detected biomedical signals by respective signals and outputting the classified signals; and a health care module for analyzing a user's emotional state and physical condition based on the biomedical signals input from the biomedical signal measurement module and user's physical information.

40 Claims, 26 Drawing Sheets

U.S. PATENT DOCUMENTS

| | | | | |
|---|---|---|---|---|
| 6,656,116 | B2 * | 12/2003 | Kim et al. | 600/300 |
| 6,881,191 | B2 * | 4/2005 | Oakley et al. | 600/483 |
| 7,261,690 | B2 * | 8/2007 | Teller et al. | 600/300 |
| 2002/0109621 | A1 * | 8/2002 | Khair et al. | 341/174 |
| 2003/0069728 | A1 * | 4/2003 | Tato et al. | 704/231 |
| 2003/0139654 | A1 | 7/2003 | Kim et al. | |

FOREIGN PATENT DOCUMENTS

| | | |
|---|---|---|
| EP | 1 183 997 A2 | 3/2002 |
| EP | 1 183 997 A3 | 6/2003 |
| JP | 7-204169 | 8/1995 |
| JP | 08-052119 | 2/1996 |
| JP | 8-052119 A | 2/1996 |
| JP | 8-112270 | 5/1996 |
| JP | 11-299740 | 11/1999 |
| JP | 2000-229072 A | 8/2000 |
| JP | 2000-358088 A | 12/2000 |
| JP | 2001-344352 | 12/2001 |
| JP | 2001-346784 A | 12/2001 |
| JP | 2002-095637 A | 4/2002 |
| JP | 2002-200051 | 7/2002 |
| JP | 2003-521972 | 7/2003 |
| KR | 2002-0011730 | 2/2002 |
| KR | 1020020011730 A | 2/2002 |
| KR | 1020020018541 A | 3/2002 |
| KR | 1020020069866 A | 9/2002 |
| KR | 2003-0063640 | 7/2003 |
| WO | 01/28416 A | 1/2001 |
| WO | WO02/33846 A1 | 4/2002 |
| WO | WO02/060380 A2 | 8/2002 |
| WO | WO02/060380 A3 | 8/2002 |

OTHER PUBLICATIONS

Rosalind W. Picard et al., "Toward Machine Emotional Intelligence: Analysis of Affective Physiological State", IEEE Transactions on Pattern Analysis and Machine Intelligence, 2001, pp. 1175-1191, vol. 23, No. 10, IEEE Computer Society, USA.

Vladimir N. Vapnik, "An Overview of Statistical Learning Theory", IEEE Transactions on Neural Networks, 1999, pp. 988-999, vol. 10, No. 5, IEEE.

R.O. Duda et al., "Pattern Classification, Bayesian Decision Theory" 2000, pp. 20-27, $2^{nd}$ Edition, Wiley & Sons.

P.M.T. Broersen, "Facts and Fiction in Spectral Analysis", 2000, pp. 766-772, IEEE Transactions on Instrumentation and Measurement, vol. 49, No. 4, IEEE.

Ronald D. Berger et al., "An Efficient Algorithm for Spectral Analysis of Heart Rate Variability", IEEE Transactions on Biomedical Engineering, 1986, pp. 900-904, vol. BME-35, No. 9, IEEE.

Korean Patent Office Notice of Examination Report of May 25, 2004 and translation.

Korean Patent Office Notice of Examination Report of Oct. 8, 2004 and translation.

Japanese Office Action and English Translation dated Jun. 22, 2005.

Japanese Office Action dated Feb. 22, 2006.

Official Action (Communication Pursuant to Article 96(2) EPC) issued in corresponding European Patent Application No. 03 256 325, Mar. 13, 2007, EPO, Munich, DE.

* cited by examiner

MOBILE DEVICE HAVING HEALTH CARE FUNCTION BASED ON BIOMEDICAL SIGNALS AND HEALTH CARE METHOD USING THE SAME

This application claims the priority of Korean Patent Application No. 10-2002-0061582 filed on Oct. 9, 2002 in the Korean Intellectual Property Office, the disclosure of which is incorporated herein in its entirety by reference.

BACKGROUND OF THE INVENTION

1. Field of Invention

The present invention relates to a mobile device capable of performing biomedical signal measurement and a health care method using the same. More particularly, the present invention relates to a mobile device capable of checking a user's state of health using a handheld mobile device mounted with a biomedical signal measurement module, which can be used both as a mobile device and in measuring biomedical signals if necessary, and a health care method using the same.

2. Description of the Related Art

As industrial societies have developed, the modern people have suffered greatly from various kinds of adult diseases such as hypertension, corpulence, diabetes and cardiac disorders due to stress from heavy workloads and lack of physical exercise, and accordingly, the death rate tends to increase every year. Such an increase of adult diseases and the resultant death rate allows modern people to gradually pay attention to their own health. Thus, devices for allowing their own health state to be examined at any time have been actively developed.

Typical health care devices capable of examining the current state of health of a user include blood pressure gauges, thermometers, body fat analyzers, and the like. These devices are widely used in a variety of fields for the purpose of medical or non-medical treatment.

However, since most of the blood pressure gauges, thermometers and body fat analyzers should be provided with additional devices to check the user's health, they are improper for portable use. Due to the inconvenience of carrying these devices, it is difficult to perform continuous health care monitoring for users.

As a device for avoiding such inconvenience of carrying extra devices, a mobile communication terminal capable of diagnosing the cardiac function of a user or checking their obesity based on heart rate and body fat percentage detected from a user's body is disclosed in Korean Patent Laid-Open Publication No. 2002-11730 (publication date: Feb. 9, 2002), as shown in FIG. 1. However, the mobile communication terminal cannot provide countermeasures for overcoming stress that may be fatal to modern people living in a highly competitive society. Furthermore, another device is required for managing a user's mental state of health as well as the physical condition of the user.

SUMMARY

The present invention is conceived to solve the problems in the related art. An object of the present invention is to provide a mobile device capable of efficiently performing health care functions for a user by checking a user's state of health using a handheld mobile device mounted with a biomedical signal measurement module, which is usually used as a mobile device and if necessary, in measuring the emotional state and physical condition of a user, and a health care method using the same.

Another object of the present invention is to provide a mobile device capable of simply checking the emotional state and physical condition of a user through the user's natural action for using a mobile device, and a health care method using the same.

In order to accomplish the above object, there is provided a mobile device with an input unit, a display unit, a memory unit and a central control unit, the mobile device according to one embodiment of the present invention comprises a biomedical signal measurement module for detecting biomedical signals from a user's body, classifying the detected biomedical signals by respective signals and outputting the classified signals; and a health care module for analyzing a user's emotional state and physical condition based on the classified signals input from the biomedical signal measurement module and user's physical information.

The biomedical signal measurement module comprises a sensor unit for detecting one or more biomedical signals from the user's body; and a sensor control unit for controlling the sensor unit, classifying the biomedical signals input from the sensor unit by the respective biomedical signals and outputting the classified biomedical signals. At this time, the sensor unit includes a heart rate sensor for detecting heartbeat-related biomedical signals and the biomedical signals of heartbeat are PPG signals.

The sensor unit includes a skin temperature sensor for detecting skin temperature-related biomedical signals, and the biomedical signals of skin temperature are SKT signals.

The sensor unit includes skin resistance sensor for detecting skin resistance-related biomedical signals. At this time, the biomedical signals of skin resistance are EDA signals.

The sensor unit includes body fat sensor for measuring body impedance required for calculation of a body fat percentage.

Each of the heart rate sensor, skin temperature sensor, skin resistance sensor and body fat sensor comprises a filter for filtering the detected biomedical signals and an amplifier for amplifying the filtered biomedical signals.

Each of the heart rate sensor, skin temperature sensor, skin resistance sensor and body fat sensor is installed at a position on the mobile device with which user's hand comes into contact when the user holds the mobile device.

The sensor control unit corrects user-to-user variation of the biomedical signals which are output from the sensor unit.

The biomedical signal measurement module is constructed to be detachably coupled to the mobile device. At this time, the biomedical signal measurement module is constructed in the form of a case capable of accommodating the mobile device therein.

The health care module comprises an emotional state analysis unit for analyzing the biomedical signals input from the biomedical signal measurement module and determining the user's emotional state; and a physical condition analysis unit for analyzing the user's physical condition based on the biomedical signals input from the biomedical signal measurement module and the user's physical information.

The emotional state analysis unit comprises a feature analysis unit for analyzing features of the biomedical signals detected from the user's body; a subtracter unit for obtaining differences between the analysis results from the feature analysis unit and feature values on the basis of which the user's emotional state is determined; and an SVM unit for analyzing the differences of the feature values obtained by the subtracter unit, classifying the user's emotional state, and calculating and outputting an index and level for a specific emotion among the classified emotions.

The feature analysis unit comprises a heartbeat analysis unit for receiving PPG signals to detect heartbeat signals and extracting feature values related to the heartbeat signals; a skin conductive response analysis unit for receiving EDA signals and extracting feature values related to a skin conductive response; and a skin temperature analysis unit for receiving SKT signals and extracting feature values related to skin temperature.

The heartbeat analysis unit comprises a heartbeat detection unit for receiving the PPG signals to detect the heartbeat signals and converting the detected heartbeat signals into time series signals of heart rate variability; a spectrum analysis unit for analyzing a spectrum of the heartbeat signals in response to the time series signals of the heart rate variability; and a mean/standard deviation calculation unit for calculating a mean value and standard deviation value of the heartbeat signals in response to the time series signals of the heart rate variability.

The heartbeat detection unit comprises a band pass filter for extracting signals falling within a specific band of the PPG signals; a median filter for removing noise existing in the filtering results of the band pass filter; an adder for calculating a difference between the filtering results of both the band pass filter and the median filter by adding a reciprocal number of the filtering result of the median filter to the filtering result of the band pass filter; a matched filter for extracting the heartbeat signals from output signals of the adder; and a zero clipper for performing zero clipping for the heartbeat signals.

The subtracter unit uses feature values of a user's normal emotion as the feature values on which the user's emotional state is determined based.

The SVM unit may comprise an SVM classifier for classifying the user's emotional state into a plurality of categories by analyzing the differences of the features values obtained from the subtracter unit; and an emotional state determination unit for selecting values related to the specific emotion among values of the plurality of emotions classified by the SVM classifier and calculating and outputting the index and level for the specific emotion. At this time, the SVM unit further comprises a database for storing a plurality of pieces of emotion data for training the SVM classifier, and trained results of the SVM classifier based on the emotion data.

The physical condition analysis unit comprises a body fat percentage calculation unit for calculating body fat percentage based on a body impedance value detected by the biomedical signal measurement module and user's height, weight, age and sex; and a calorie consumption calculation unit for calculating calorie consumption due to exercise based on average heart rates and body fat percentages before/after exercise detected by the biomedical signal measurement module.

In order to accomplish the above object, a health care method using a mobile device, comprises the steps of detecting biomedical signals from a user's body; classifying the detected biomedical signals by respective signals; analyzing the user's emotional state and physical condition based on the classified signals and user's physical information.

The health care method further comprises the steps of selecting, by a user, a health care menu on a mobile device with a biomedical signal measurement module; if the user selects emotional state measurement, activating the biomedical signal measurement module to detect the biomedical signal in the mobile device.

The step of analyzing the user's emotional state and physical condition comprises the steps of analyzing the detected biomedical signals and extracting a plurality of feature values to be used for determining user's emotional state; calculating differences between the plurality of extracted feature values and feature values on the basis of which the user's emotional state is determined; classifying the user's emotional state by respective emotions based on SVM classification according to the calculated differences of the feature values.

The health care method further comprises the step of selecting values related to an emotion selected among the classified emotions, calculating an emotional state index and level for the selected emotion, and displaying the calculated emotional state index and level on a display unit of the mobile device.

The biomedical signals detected from the user's body include biomedical signals of heartbeat. At this time, the biomedical signals of heartbeat are PPG signals.

The biomedical signals detected from the user's body include skin temperature-related biomedical signals. At this time, the biomedical signals of skin temperature are SKT signals.

The biomedical signals detected from the user's body include skin resistance-related biomedical signals. At this time, the biomedical signals of skin resistance are EDA signals.

The biomedical signals detected from the user's body are filtered by a filter and then amplified by an amplifier.

The health care method further comprises the step of correcting user-to-user variation of the biomedical signals detected from the user's body.

The step of correcting the user-to-user variation of the biomedical signals comprises the steps of determining whether the user's body is in contact with the biomedical signal measurement module; if it is determined that the user's body is in contact with the biomedical signal measurement module, determining whether the correction of the user-to-user variances of the detected biomedical signals is required; if it is determined that the correction of the user-to-user variances of the detected biomedical signals is required, checking whether values of the detected biomedical signals are above a maximum limit level and decreasing a gain of an amplifier if the values of the detected biomedical signals are above the maximum limit level; and if the values of the detected biomedical signals are equal to or less than the maximum limit level, checking whether the values of the detected biomedical signals are equal to or less than a minimum limit level and increasing the gain of the amplifier if the values of the detected biomedical signals are equal to or less than the minimum limit level.

The step of analyzing the biomedical signals and extracting the plurality of feature values to be used for determining the user's emotional state comprises the steps of receiving PPG signals to detect heartbeat signals and extracting feature values related to the heartbeat signals; receiving EDA signals and extracting feature values related to a skin conductive response; and receiving SKT signals and extracting feature values related to skin temperature.

The feature values on the basis of which the user's emotional state is determined are feature values of user's normal emotion.

The step of classifying the user's emotional state by the respective emotions uses an SVM classifier that classifies the user's emotional state into a plurality of categories based on a statistical learning theory.

The biomedical signal measurement module is configured to be detachably coupled to the mobile device. At this time, the biomedical signal measurement module is constructed in the form of a case capable of accommodating the mobile device therein.

The health care method further comprises the steps of, if the user selects body fat measurement, activating a body fat sensor in the biomedical signal measurement module mounted to the mobile device; measuring body impedance from the user's body by the body fat sensor; and calculating a body fat percentage of the user's body based on the measured impedance and user's physical information and displaying the calculated the body fat percentage on the display unit.

The health care method further comprises the steps of, if the user selects calorie consumption measurement, activating a heart rate sensor and a body fat sensor in the biomedical signal measurement module; measuring heartbeat signals and body impedance before/after exercise from the user's body by the heart rate sensor and the body fat sensor; and analyzing the heartbeat signals and the body impedance before/after exercise to calculate average heart rates and body fat percentages before/after exercise, calculating calorie consumption due to exercise based on the calculated average heart rates and body fat percentages before/after exercise, exercise time, and user's physical information, and displaying the calculated calorie consumption on the display unit.

The health care method further the step of, if the user selects history management, displaying measurement results according to respective desired terms on the display unit.

BRIEF DESCRIPTION OF THE DRAWINGS

The above and other objects and features of the present invention will become apparent from the following description of a preferred embodiment given in conjunction with the accompanying drawings, in which.

DESCRIPTION

Hereinafter, a preferred embodiment of a mobile device and a health care method according to the present invention will be described in detail with reference to the accompanying drawings.

Figure 1:
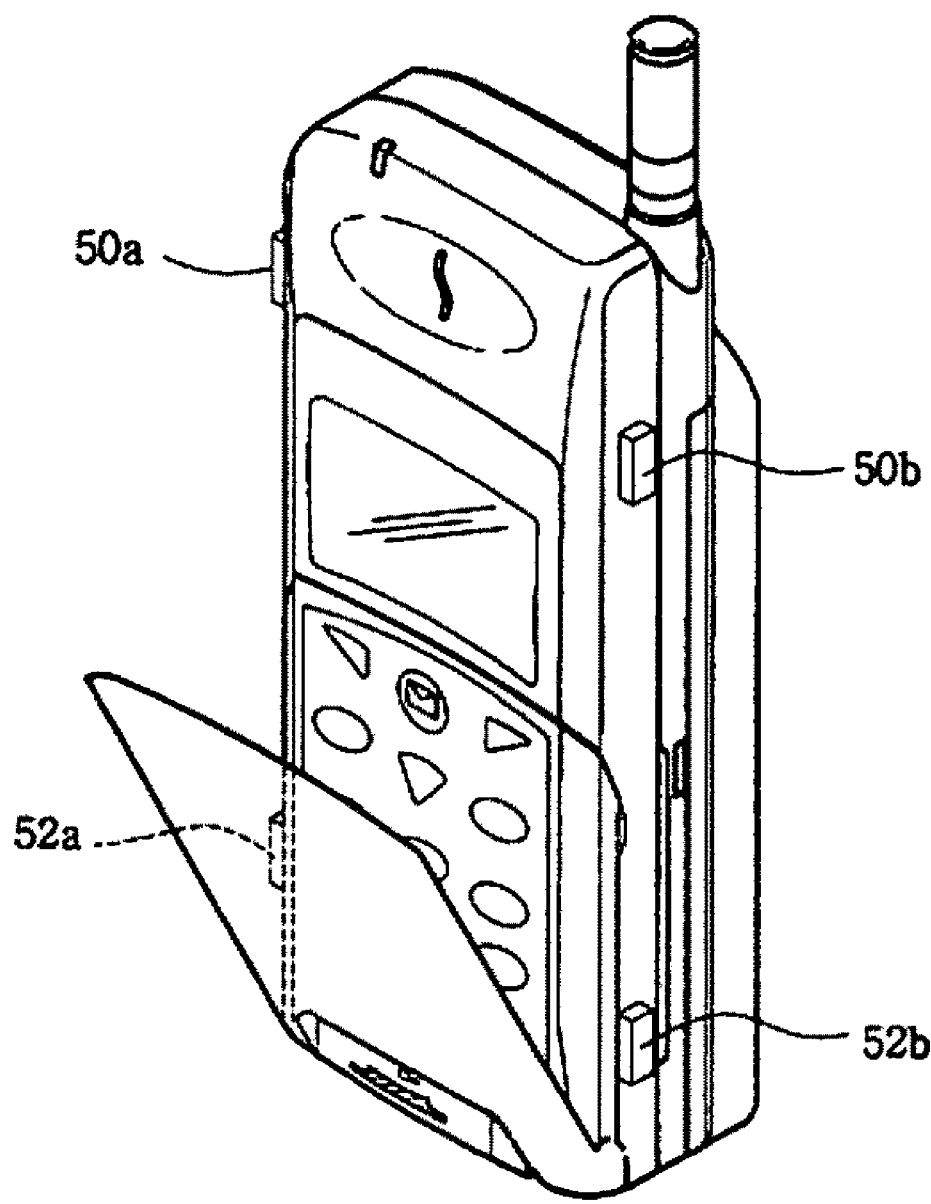
FIG. 1 is a view of a mobile communication terminal with a conventional biomedical information measurement module included therein.
Figure 2:
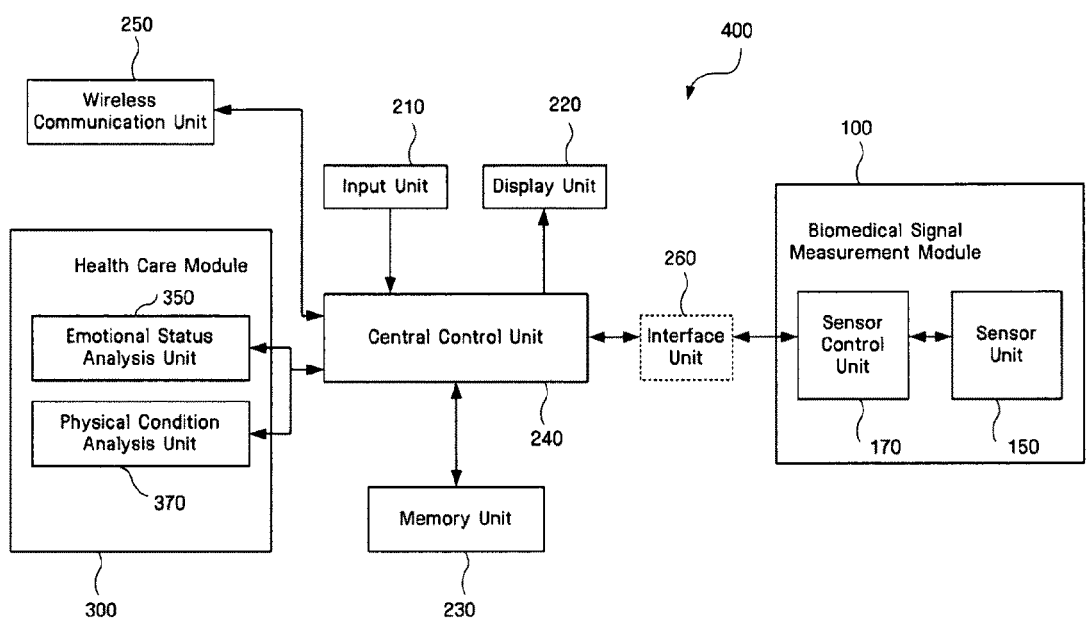
FIG. 2 is a block diagram schematically illustrating a mobile device according to the present invention.

FIG. 2 is a block diagram schematically illustrating a configuration of the mobile device according to the present invention. As shown in FIG. 2, the mobile device 400 of the present invention comprises a biomedical signal measurement module 100, an input unit 210, a display unit 220, a memory unit 230, a central control unit 240, and a health care module 300. The mobile device is configured such that it can be easily used both as a mobile device and as a device that can check the state of health of a user, if necessary, through the biomedical signal measurement module 100 and the health care module 300.

The mobile device 400 of the present invention can be used as a wireless communication device. In such a case, the mobile device of the present invention further comprises a wireless communication unit 250 capable of transmitting and receiving voice and characters by radio. Therefore, it can be understood in the embodiment of the present invention that the mobile device 400 can be any of the following, or similar, portable electronic equipment such as PDA (Personal Digital Assistants), Palm-Top PC, handheld PC, PCS (Personal Communication Service) phone, cellular phone, and IMT-2000 terminal.

Further, other external devices can be used with and connected to the mobile device 400 of the present invention. In such a case, the mobile device 400 can further include an interface unit 260 for transmitting and receiving data to and from external devices.

The biomedical signal measurement module 100 includes a sensor unit 150 for detecting one or more biomedical signals from the body of a user, and a sensor control unit 170 for controlling the sensor unit 150 or classifying and outputting the biomedical signals input from the sensor unit 150.

The input unit 210 is used to input numbers, symbols and characters such as the Korean and English alphabets through a keypad, scroll buttons, numeric pad and the like. At this time, the user can use a variety of functions such as the input of numerals and symbols of telephone numbers, and start and completion of a telephone call, through the input unit 210, when intending to use the mobile device as it is. Furthermore, the user can input his/her height, weight, age, sex, and the like through the input unit 210 when intending to use the mobile device as a health care device.

The display unit 220 displays either numbers/characters the user inputs or biomedical signal data of the user measured from the biomedical signal measurement module 100 onto a screen.

The memory unit 230 stores information on the user's body, directions for use of the mobile device, and general health information in addition to a variety of data including telephone numbers.

The central control unit 240 controls an overall operation of the mobile device 400. That is, the central control unit 240 measures biomedical signals through the biomedical signal measurement module 100 if necessary, and then analyzes the measured biomedical signal using the health care module 300 so as to check the state of health of the user.

The wireless communication unit 250 functions to transmit and receive voice and character data by radio and has the same constitution and operation as that used generally in the field of wireless communication terminals. Therefore, a detailed description thereof will be omitted.

The interface unit 260 receives data from external devices connected to the mobile device and outputs the input data to the central control unit 240, and functions to output the biomedical signals from the user input by the biomedical signal measurement module 100 to the central control unit 240 in a case where the biomedical signal measurement module 100 is mounted to the mobile device. At this time, the interface unit 260 transmits and receives the signal to and from the biomedical signal measurement module 100 through the use of a communication protocol such as RS232C. This is merely an example of a signal transmission method, and a variety of communication protocols can be used depending on the circuit configuration.

The configuration of the biomedical signal measurement module 100 will be more specifically explained with reference to FIG. 3.

Figure 3:
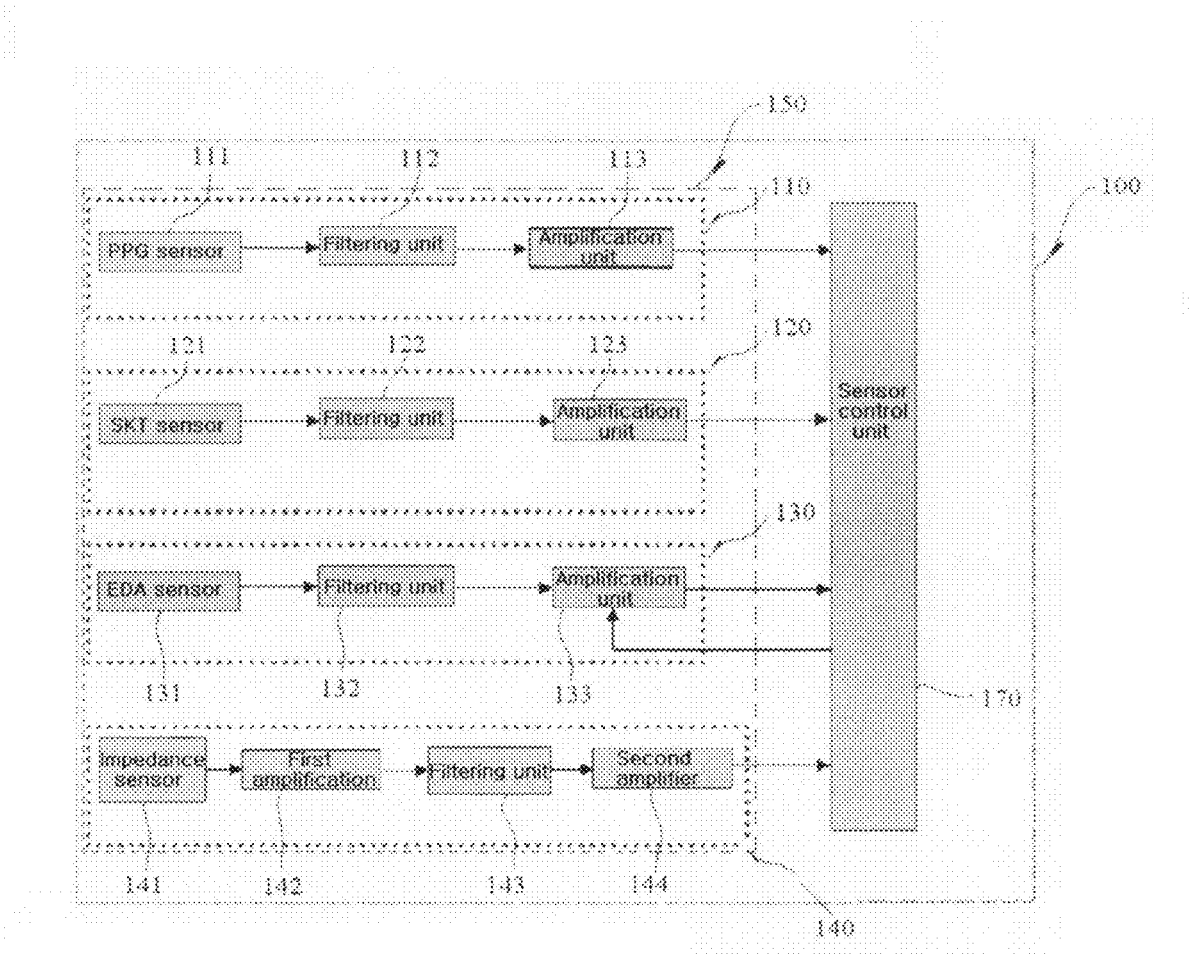
FIG. 3 is a view showing an interior configuration of a biomedical signal measurement module of the mobile device shown in FIG. 2.

FIG. 3 shows an interior configuration of the biomedical signal measurement module 100 shown in FIG. 2. As shown in FIG. 3, the biomedical signal measurement module 100 includes the sensor unit 150 for detecting one or more biomedical signals from the body of a user, and the sensor control unit 170 for controlling the sensor unit 150 or classifying and outputting the biomedical signals input from the sensor unit 150.

Generally, in a stable mental state, a user's heartbeat becomes slow and peripheral blood vessels are expanded. Therefore, the user's body temperature at the skin and thus skin resistance are increased. However, if the user is excited or subjected to stress, the heartbeat becomes fast and the blood moves from the skin to muscles. Therefore, the user's body temperature and thus the skin resistance tend to be decreased. Consequently, such changes in heartbeat, skin temperature and skin resistance are deemed to be an important factor for determining the stress level of the user.

In the embodiment of the present invention, accordingly, the heartbeat, skin temperature and skin resistance, which quickly respond to the user's skin according to an emotional change, are measured in order to check the stress level of the user. To this end, the sensor unit 150 of the biomedical signal measurement module 100 includes a heart rate sensor 110 for detecting a biomedical signal for heartbeat, a skin temperature sensor 120 for detecting a biomedical signal for skin temperature, and a skin resistance sensor 130 for detecting a biomedical signal for skin resistance.

In the embodiment of the present invention, it is preferred that the heartbeat sensor include a PPG (photoelectric pulse plethysmograph) sensor 111 for measuring changes in blood flow according to a change in the thickness of blood vessel due to the heartbeat. It is also preferred that the skin temperature sensor 120 include an SKT sensor 121 such as a thermistor for measuring skin temperature (SKT) as a resistance value that changes in response to temperature change. Further, it is preferred that the skin resistance sensor 130 include an EDA (electrodermal activity) sensor 131 for measuring skin resistance that changes under the influence of sweat eliminated from the skin by using an electrode directly or indirectly in contact with the skin and a comparator connected with the electrode. Preferably, the skin resistance sensor 130 may include a galvanic skin resistance (GSR) sensor for measuring galvanic skin resistance instead of the EDA sensor.

According to a preferred embodiment of the present invention, the heart rate sensor 110, the skin temperature sensor 120 and the skin resistance sensor 130 include filters 112, 122 and 132 for filtering the detected biomedical signals and amplifiers 113, 123 and 133 for amplifying the filtered biomedical signals, respectively.

In the meantime, since user-to-user variation in biomedical signals detected through the sensor unit 150 largely changes depending on response sensitivity and measuring environment, the stress level of the user may not be measured exactly.

Figure 4:
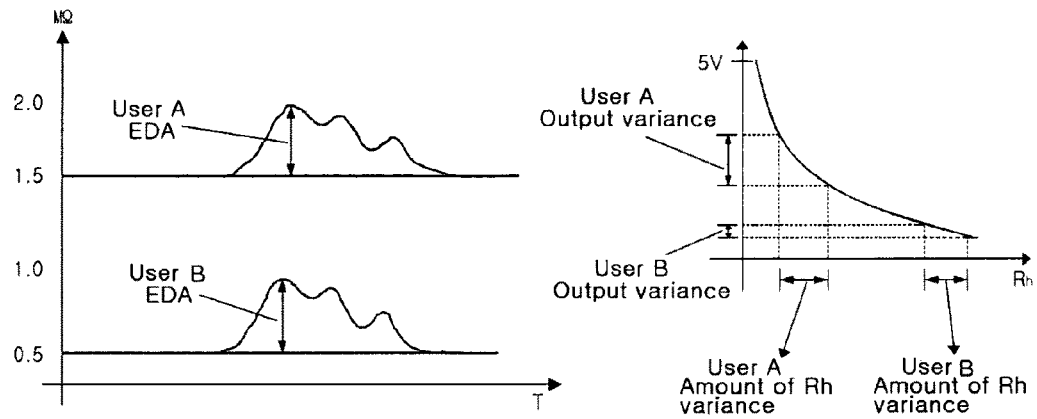
FIG. 4 is a graph plotting waveforms of EDA signals measured by a skin resistance sensor unit of FIG. 3.

Specifically, a nickel electrode is employed in the EDA sensor 131 of the skin resistance sensor 130 so that skin resistance $R_h$ of the user can be measured for a long time. In such cases, the nickel electrode has an advantage in that it is superior to conventional Ag/AgCl electrodes in view of their durability, but has a problem in that user-to-user variation in a DC value of the skin resistance $R_h$ detected through the nickel electrode is increased. As shown in FIG. 4, for example, it is assumed that a person A has a dry skin of which skin resistance $R_h$ is between 1.5~2.0 MΩ whereas a person B has wet and sweaty skin of which skin resistance $R_h$ is between 0.5~1.0 MΩ. Therefore, if there is such variation in the skin resistance $R_h$, it is deemed that the emotional state of the user is not properly reflected. Accordingly, it is necessary to correct user-to-user variation in skin resistance during the initialization stage of measurement.

To this end, the sensor control unit 170 of the biomedical signal measurement module 100 corrects user-to-user variation in skin resistance by decreasing or increasing the gain of the amplifier 133 according to the voltage value $V_0$ output from the EDA sensor 131 through the amplifier 133. Hereinafter, the variation correction of the sensor control unit 170 will be explained in detail with reference to FIG. 5.

Figure 5:
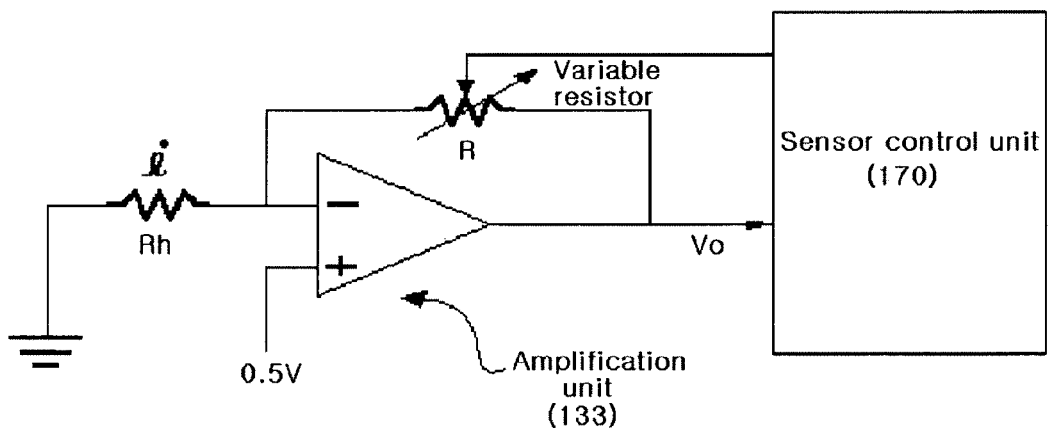
FIG. 5 is a view illustrating how to correct user-to-user variation of the EDA signal, which is measured through the skin resistance sensor unit of FIG. 3.

As shown in FIG. 5, assuming that an electric current measured in the EDA sensor 131 is i, the skin resistance of the user is $R_h$ and variable resistance for controlling the gain of the amplifier 133 is R, the voltage value $V_0$ input into the sensor control unit 170 can be expressed as the following formula.

$$V_0 = (R_h + R) \times i = (R_h \times i) + (R \times i),$$

where $(R_h \times i) = 0.5V$.

The above formula can also be expressed as follows.

$$V_0 = 0.5 \times \frac{R}{R_h}$$

Therefore, the relationship $V_0 \propto R$ is satisfied. That is, the voltage value $V_0$ input into the sensor control unit 170 is proportional to the value R of the variable resistor. Accordingly, the voltage $V_O$ is decreased as the resistance value R of the variable resistor is decreased, whereas the voltage $V_O$ is increased as the value R of the variable resistor is increased.

In accordance with this principle, when the input voltage value $V_O$ is equal to or greater than an upper limit voltage, the sensor control unit 170 reduces the value R of the variable resistor and thus the gain of the amplifier 133, thereby reducing the voltage $V_O$. On the other hand, when the input voltage $V_O$ is equal to or less than a lower limit voltage, the sensor control unit 170 increases the value R of the variable resistor and thus the gain of the amplifier 133, thereby increasing the voltage value $V_O$.

Accordingly, the voltage value $V_O$ output from the amplifier 133 can be maintained between the lower limit voltage and the upper limit voltage by means of the correction of the sensor control unit 170 for the user-to-user variation. Consequently, the biomedical signal onto which variation in the emotional state of the user is properly reflected can be detected.

Although heartbeat, temperature and skin resistance as response factors for determining the emotional state of a user have been measured in the embodiment of the present invention, any one or two factors of these biomedical signals may be measured. However, it is preferred that all the three factors be measured in order to determine the emotional state of the user more accurately.

Referring again to FIG. 3, the sensor unit 150 of the biomedical signal measurement module 100 further includes a body fat sensor unit 140 for measuring body impedance necessary to calculate body fat percentage so as to measure the body fat of the user.

The body fat percentage is referred to as a percentage of fat in the body. Appropriate body fat is essentially required for protecting body organs, shielding heat from being emitted, and maintaining body temperature. However, excessive body fat hinders smooth metabolism, and thus, becomes a primary factor for increasing aging phenomena and diseases of adult people such as hyperlipemia, sclerosis of the arteries, hypertension, and diabetes. Accordingly, it is very important to keep the body fat percentage at an appropriate level in order to preserve the user's health.

The body fat sensor unit 140 includes an impedance sensor 141 for measuring body impedance by causing a small alternating current to flow through the electrode in contact with the body surface of the user and then measuring the voltage between both ends of the electrode. Body impedance measured by the impedance sensor 141 is first amplified by a first amplifier 142, is then filtered through a filter 143, and is again amplified by a second amplifier 144. Thereafter, the body impedance is input into the sensor control unit 170.

The body fat percentage can be calculated according to the impedance method based on the body impedance measured in the body fat sensor 140 and information on the user's body (sex, age, height, weight). The impedance method is a method of measuring electrical resistance in the body and thus calculating body fat percentage based on the principle that electricity flows easily through fat-free tissues of the body since fat-free tissues contain a great deal of moisture (72~73% including electrolyte), whereas fat tissues are insulated so electricity does not flow through fat tissues since fat tissues contain significantly less moisture.

Furthermore, it is preferred that the biomedical signal measurement module 100 be configured such that it can be efficiently carried and easily used for measurement. Hereinafter, a process of implementing the biomedical signal measurement module 100 will be explained in detail with reference to FIGS. 6 to 8.

Figure 6:
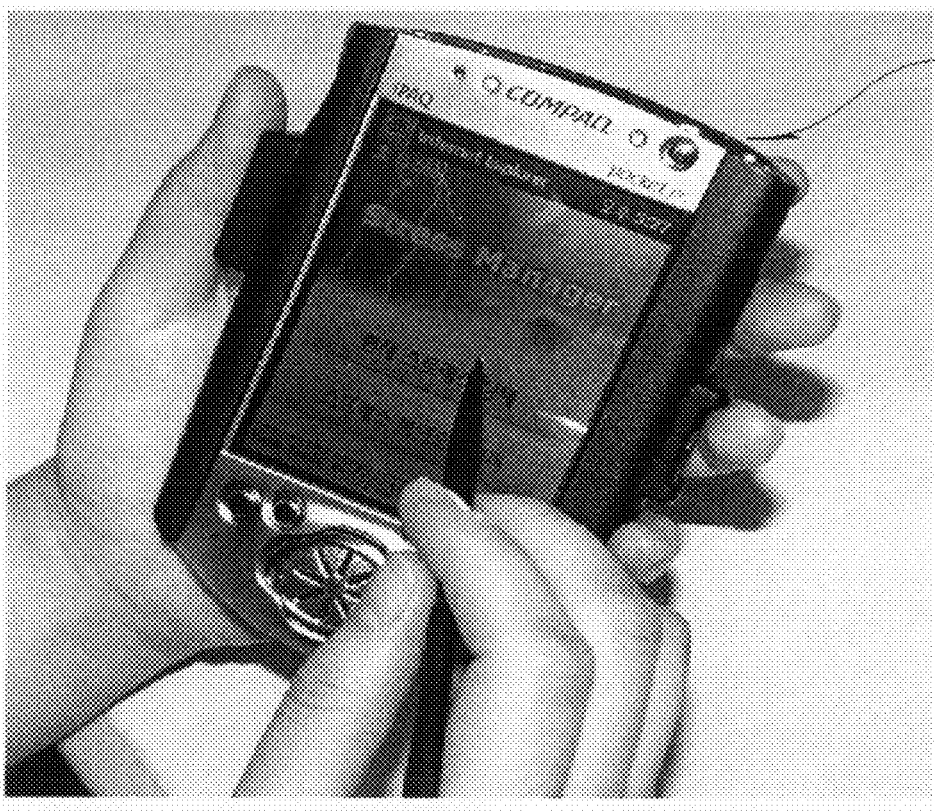
FIG. 6 is a view showing an embodiment of a mobile device according to the present invention.
Figure 7:
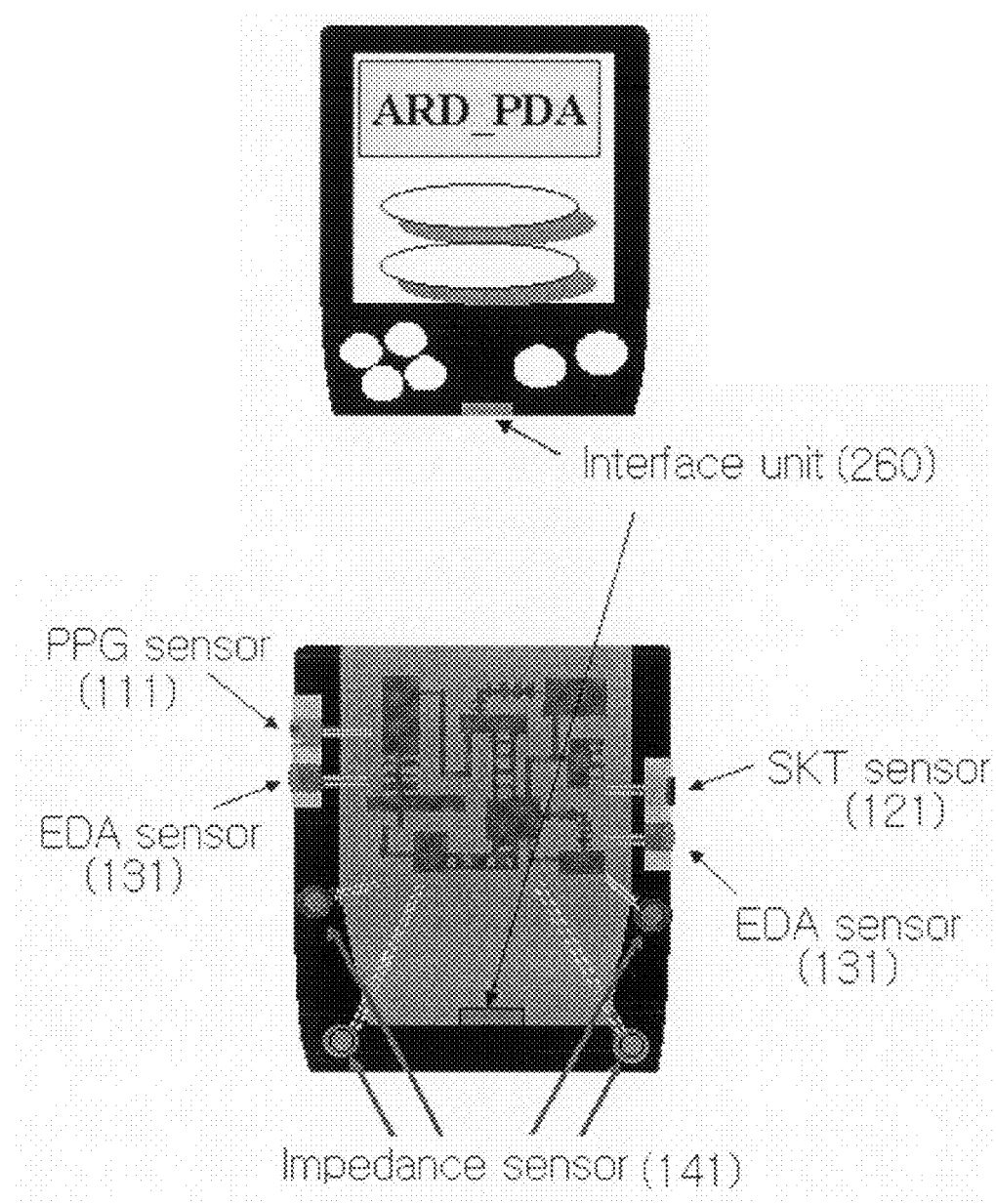
FIG. 7 is a view illustrating a state where the biomedical signal measurement module is separated from the mobile device shown in FIG. 6.
Figure 8:
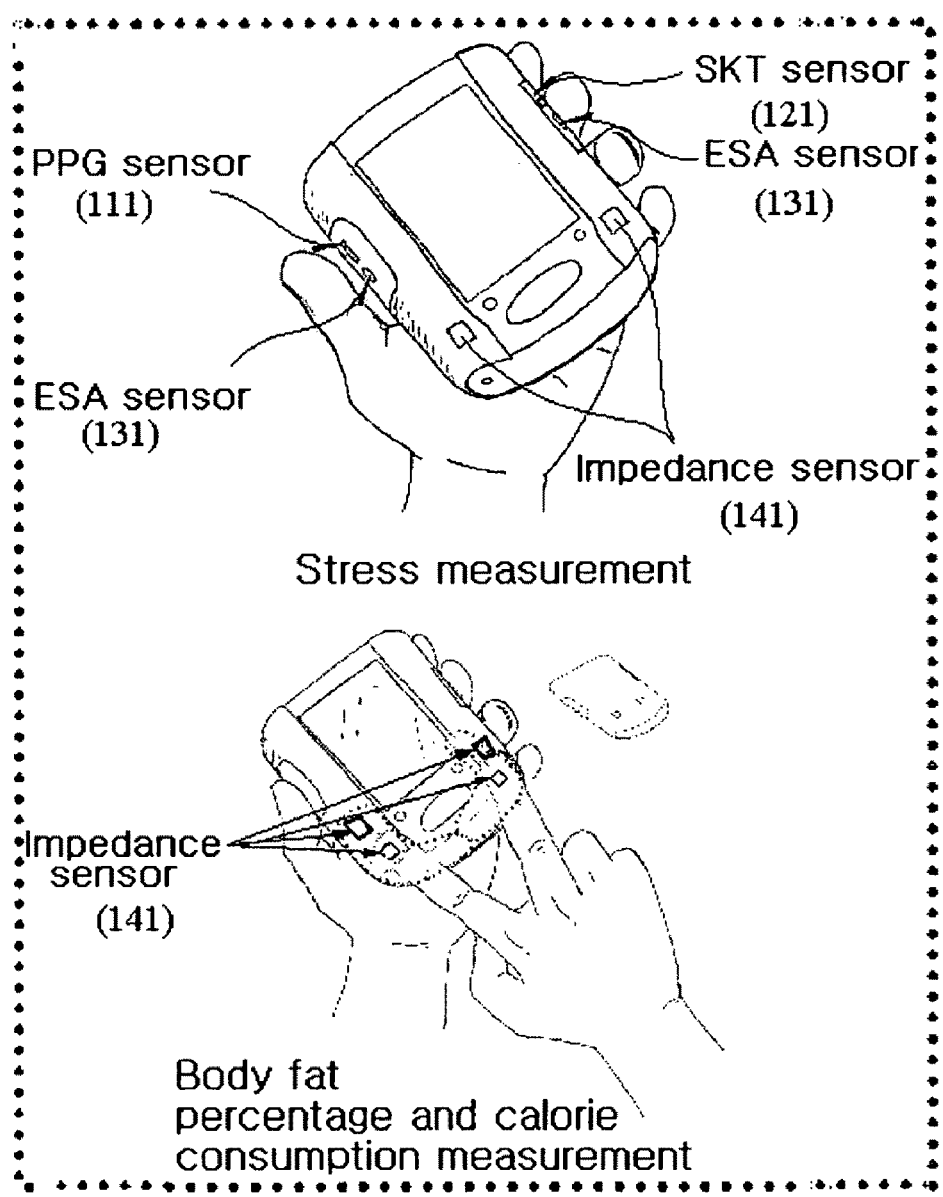
FIG. 8 is a view illustrating how to measure biomedical signals using the mobile device according to the present invention.

FIG. 6 is a view showing an embodiment of the mobile device according to the present invention; FIG. 7 is a view illustrating a state where the biomedical signal measurement module is separated from the mobile device shown in FIG. 6; FIG. 8 is a view illustrating how to measure biomedical signals using the mobile device according to the present invention.

It is preferred that the biomedical signal measurement module 100 be configured to be detachably mounted to the mobile device so that it can be easily carried by the user. For example, the module 100 may be configured in the form of a case with a receiving space in which the mobile device can be accommodated as shown in FIGS. 6 and 7.

In case of a case-shaped biomedical signal measurement module 100, it is preferred that a whole external appearance of the biomedical signal measurement module 100 be a shape corresponding to that of the mobile device and a front portion thereof is open such that the display unit 220 can be exposed outwardly. When the mobile device is inserted into the case-shaped biomedical signal measurement module 100, the mobile device is firmly engaged with the biomedical signal measurement module 100 while they are electrically connected with each other through the interface unit 260.

In addition, the biomedical signal measurement module 100 may be configured in the form of an additional necklace and be detachably mounted to the mobile device. Alternatively, the biomedical signal measurement module 100 may be configured to be fully housed in the mobile device.

As shown in FIGS. 7 and 8, it is preferred that the PPG sensor unit 111 of the biomedical signal measurement module 100 be arranged at a position on which a thumb of the user is placed when the user naturally holds the mobile device 400, the SKT sensor 121 thereof be arranged at a position where an index or middle finger would be placed, and the EDA sensor 131 thereof be arranged at a position just below the PPG sensor 111 and the SKT sensor 121, that is, positions where lower portions of the thumb and index or middle finger are placed when the user naturally holds the mobile device 400, such that the biomedical signal measurement module 100 can be efficiently utilized for measurement. Further, it is preferred that two electrodes of the impedance sensor 141 are installed at a rear side of the biomedical signal measurement module 100 and the other two electrodes are installed at a front side of the biomedical signal measurement module 100 so that the two rear electrodes are in contact with the palm of the user and the two front electrodes are in contact with the fingers (e.g., index or middle finger) when the user holds the mobile device 400.

Therefore, since the fingers or palm of the user can be in contact with the PPG sensor 111, the SKT sensor 121, the EDA sensor 131 and the impedance sensor 141 whenever the user merely holds the mobile device 400, the biomedical signals of the user can be conveniently detected through a natural holding action of the user.

Referring again to FIG. 2, the health care module 300 functions to analyze the emotional and physical condition of the user based on information on the user's body and the biomedical signal data input from the biomedical signal measurement module 100. The health care module 300 will be hereinafter explained in detail with reference to FIG. 9.

Figure 9:
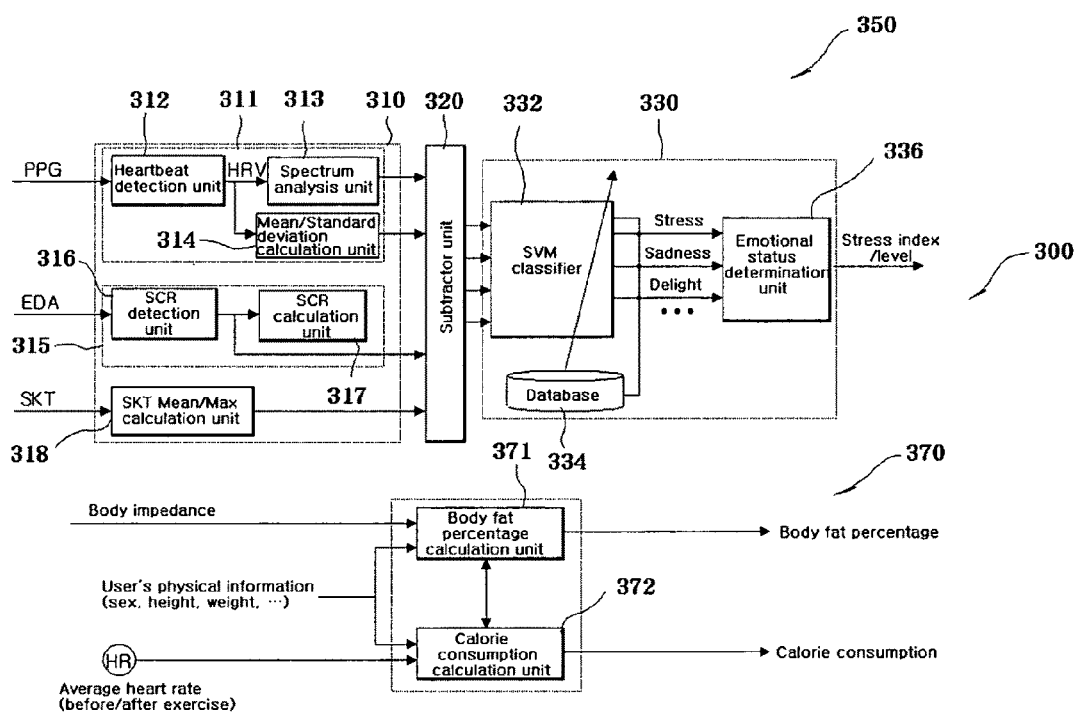
FIG. 9 is a view showing an interior configuration of a health care module shown in FIG. 2.

FIG. 9 shows an interior configuration of the health care module 300 shown in FIG. 2. As shown in FIG. 9, the health care module 300 comprises an emotional state analysis unit 350 and a physical condition analysis unit 370 for analyzing the emotional and physical condition of the user, respectively, based on the biomedical signal data input from the biomedical signal measurement module 100 and the information on the user's body stored in the memory unit 230.

The emotional state analysis unit 350 functions to analyze features of the biomedical signals measured from the user's body, recognizing emotions based on values between the analysis results and the features representing the user's normal emotion, and then outputting a stress index and level based on the recognized emotion. Such an emotional recognition algorithm is specifically described in Korean Patent Application No. 2002-3868 (entitled "device and method for recognizing a user's emotion through short monitoring of physiological signals") and will be explained briefly for easy understanding of the present invention.

The emotional state analysis unit 350 includes a feature analysis unit 310 for analyzing the features of the biomedical signals measured by the biomedical signal measurement module 100, a subtracter unit 320 for calculating a difference value between the results analyzed in the feature analysis unit and the features representing the user's normal emotion, and a support vector machine (SVM) unit 330 for classifying the emotional states according to the analyzed difference between the features calculated in the subtracter unit 320 and outputting the calculated index and level for the selected emotional state among the classified emotional states.

The feature analysis unit 310 includes a heartbeat analysis unit 311 for receiving PPG signals, detecting the heartbeat and extracting the feature values related to the heartbeat, a skin conductive response (SCR) analysis unit 315 for receiving the EDA signals and extracting feature values related to SCR, and an SKT Mean/Max calculation unit 318 for receiving the EDA signals and extracting feature values related to SKT (i.e., mean (Mean) and maximum value (Max) of SKT).

The heartbeat analysis unit 311 includes a heartbeat detection unit 312 for receiving the PPG signals and detecting the heartbeat, a spectrum analysis unit 313 for analyzing the spectrum of the detected heartbeat signal (Det), and a Mean/Std calculation unit 314 for calculating the mean (Mean) and standard deviation (Std) of the detected heartbeat signal (Det). In addition, the SCR analysis unit 315 includes an SCR detection unit 316 for receiving EDA signals and detecting SCR, and an SCR calculation unit 317 for calculating parameters such as amplitude of SCR.

Figure 10:
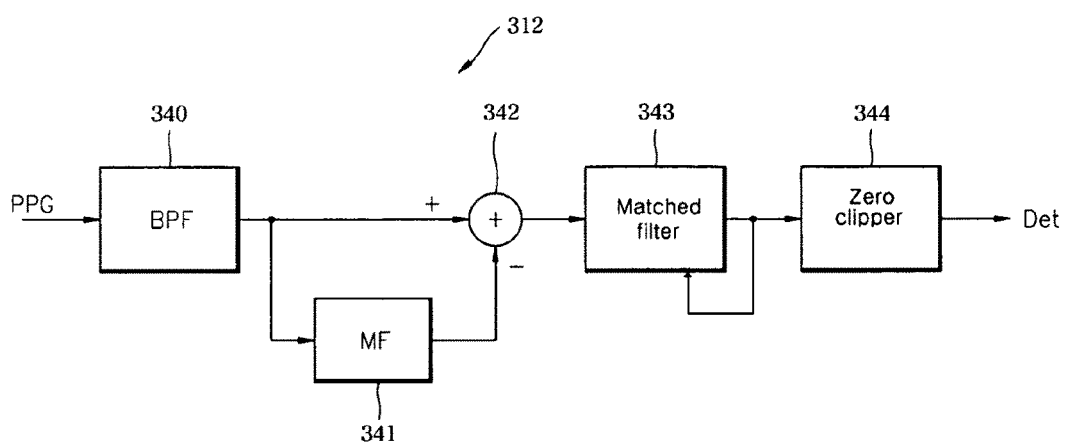
FIG. 10 is a view showing a detailed configuration of a heartbeat detection unit shown in FIG. 9.
Figure 11:
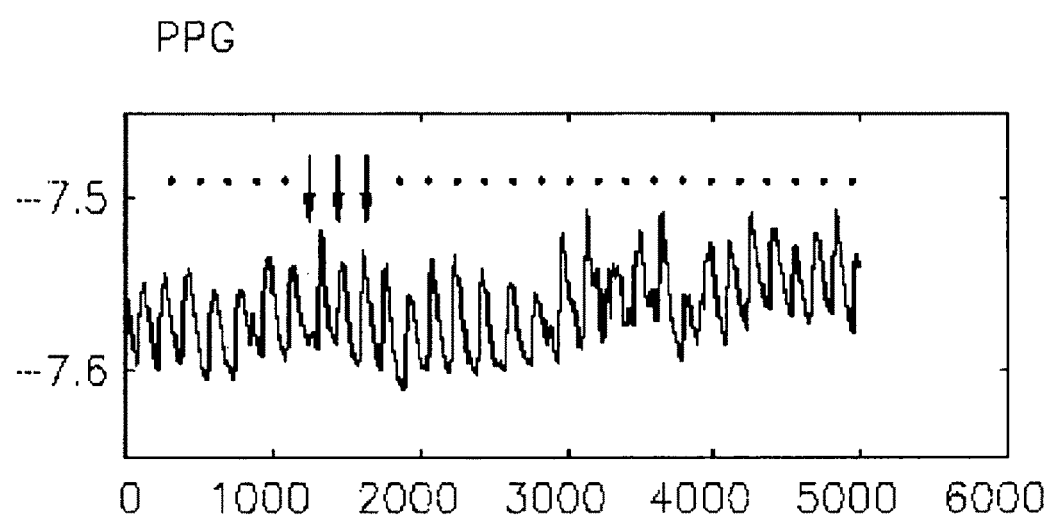
FIG. 11 is a view showing an example of a PPG signal to be used in the analysis of a heartbeat signal.

FIG. 10 is a view showing a detailed configuration of a heartbeat detection unit 312 shown in FIG. 9, and FIG. 11 is a view showing an example of the PPG signal to be used in the analysis of the heartbeat signal.

As shown in FIG. 10, the heartbeat detection unit 312 of the present invention includes a band pass filter 340, a median filter 341, an adder 342, a matched filter 343, and a zero clipper 344.

The band pass filter 340 extracts signals falling within a specific band of the PPG signal when the PPG signal is input. The median filter 341 removes noise existing in the band-pass filtered signal. The adder 342 adds a reciprocal number of the median filtered result to the band pass filtered result and calculates the difference between the two filtered results. The difference calculated through the adder 342 is input to the matched filter 343 to extract a specific signal (i.e., heartbeat signal) included in the PPG signal. The specific signal extracted from the matched filter 343 is subjected to a zero clipping process in the zero clipper 344 and is then output as the heartbeat signal (Det). Here, parameters of the matched filter 343 can be updated, if necessary. With a heartbeat detection unit 312 constructed as such, the PPG signal corresponding to portions indicated by arrows shown in FIG. 11 are extracted as the heartbeat signal (Det).

Figure 12:
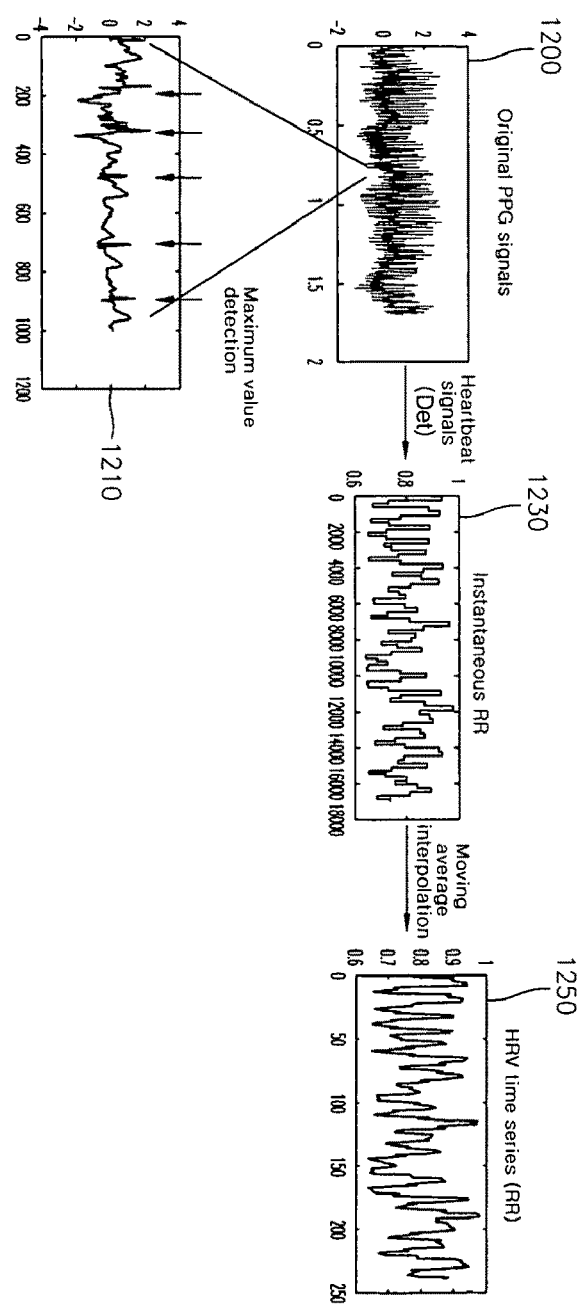
FIG. 12 is a view showing a process of obtaining time series data of a heart rate from a heartbeat signal produced by the heartbeat detection unit shown in FIG. 11.

FIG. 12 is a view showing a process of obtaining time series data of heart rate variability from a heartbeat signal produced by the heartbeat detection unit 312 shown in FIG. 11.

Referring to FIG. 12, if an obtained PPG signal 1200 is magnified, a waveform such as a waveform 1210 is illustrated. The PPG signal is shown to have periodic pulses designated by reference numeral 1210, each of which represents a QRS waveform composed of a maximum portion R and minimum portions Q and S located to the right and left of the maximum portion R, respectively.

Portions indicated by arrows among the waveform 1210 shown in FIG. 12 become an R waveform corresponding to the maximum portion of the heartbeat signal, and they are extracted through the heartbeat detection unit 312 shown in FIG. 10 to illustrate an R-R instantaneous waveform 1230 of the PPG signal. If a moving average interpolation is applied to the R-R instantaneous waveform 1230, time series data of heart rate variability (HRV) such as 1250 are extracted. A method of obtaining time series data 1250 of such heart rate variability is disclosed in the technical paper "An efficient algorithm for the spectral analysis of heart rate variability" by R. D. Berger etc. IEEE Trans. Biomed. Eng., vol. 33, 1986. The heart rate variability (HRV) signal becomes an index that can be used to quantitatively determine the degree of activation of sympathetic and parasympathetic systems.

Referring again to FIG. 9, the heartbeat signal (Det) obtained by the heartbeat detection unit 312 shown in FIG. 10 is transformed into a time series of heart rate variability (HRV) by means of the method illustrated in FIG. 12, and is then input into the spectrum analysis unit 313 and the Mean/Std calculation unit 314.

The spectrum analysis unit 313 estimates various orders of autoregressive (AR), moving average (MA), and autoregressive moving average (ARMA) models for the given time series, selects an optimal time series model by choosing a specific order of a specific model of which an index for representing estimated error can be minimized, and analyzes the spectrum of heart rate variability (HRV) using an ARMAsel algorithm for obtaining the spectrum from the selected optimal model. A method of estimating an index for an estimated error and a time series model is specifically described in the technical paper "Fact and fiction in spectral analysis" by P. M. T. Broersen, IEEE Transactions on instrumentation and measurement, vol. 49, no. 4, pp. 766-772, 2000.

The frequency domain parameters of such heart rate variability (HRV) have been studied as an important index in many previous research efforts, and are also a very important index in biopsychology research.

The spectrum analysis unit 313 of the present invention analyzes the spectrum of heart rate variability (HRV) through signal observation for a short time of about 50 seconds by using the ARMAsel algorithm instead of a conventional periodogram method for long-term signals ranging from a few minutes to 24 hours. The results analyzed by the spectrum analysis unit 313 are transmitted to the subtracter unit 320 as feature values for determining the emotional state of the user.

Further, the Mean/Std calculation unit 314, which has received the time series signal of heart rate variability (HRV) from the heartbeat detection unit 312, calculates the mean (Mean) and standard deviation (Std) for the given time series and transmits the calculated values to the subtracter unit 320 as feature values for determining the emotional state of the user.

Next, the detailed configuration and operation of the SCR analysis unit 315 included in the feature analysis unit 310 of FIG. 9 will be explained as follows.

Figure 13:
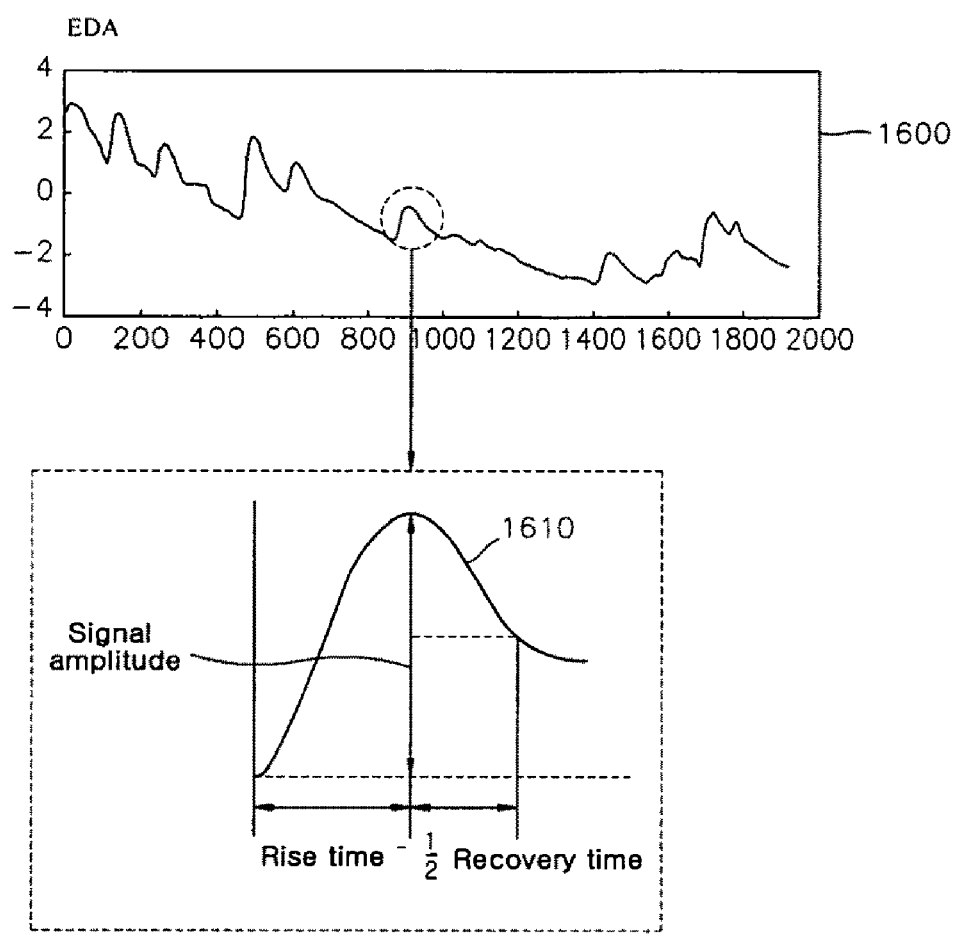
FIG. 13 is a graph showing a waveform of the EDA signal used to detect skin conductive response (SCR)

FIG. 13 is a graph showing the waveform of an EDA signal used to detect skin conductive response (SCR). FIG. 13 shows the waveform 1600 of an EDA signal generated from the user and an enlarged waveform 1610 for a portion of the EDA signal waveform 1600 from which SCR features are extracted. The signals indicated by 1600 and 1610 are input into the SCR detection unit 316 of the SCR analysis unit 315.

Figure 14:
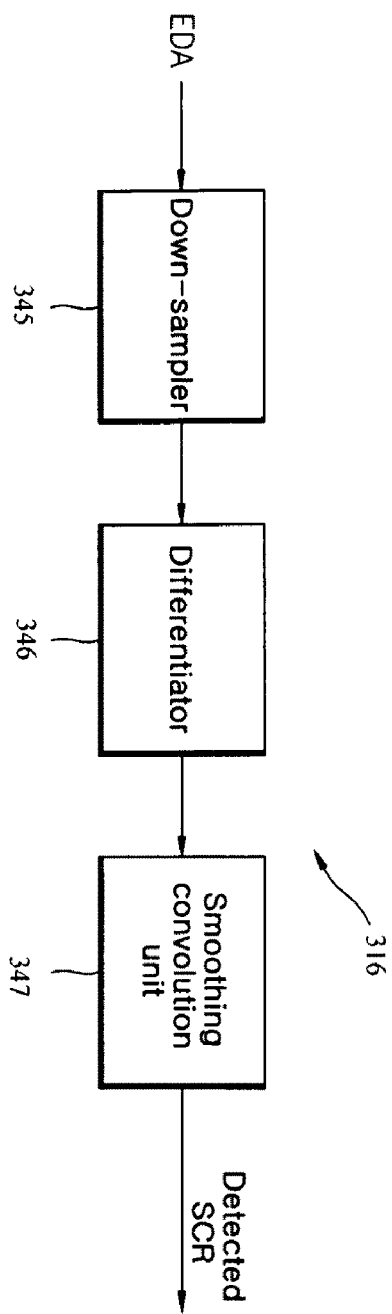
FIG. 14 is a view showing a configuration of an SCR detection unit shown in FIG. 9.

FIG. 14 is a view showing a configuration of the SCR detection unit 316 shown in FIG. 9.

Referring to FIG. 14, the SCR detection unit 316 for receiving EDA signals and detecting skin conductive response (SCR) includes a down-sampler 345, a differentiator 346, and a smoothing convolution unit 347.

The down-sampler 345 causes the input EDA signal to be down sampled to 10~12 data. The differentiator 346 differentiates the down sampled result, and the smoothing convolution unit 347 performs the smoothing convolution for the differentiated results using a Bartlett window with a length of 20. Such an SCR detection unit 316 causes the input EDA signal to be output in the form of discrete SCR data.

The discrete SCR data acquired by the SCR detection unit 316 is input to the SCR calculation unit 317 included in the SCR analysis unit 315 so that feature values such as the frequency of SCR for a predetermined period of time, SCR amplitude and SCR rise time can be produced. The SCR feature data (i.e., the frequency of SCR, the SCR amplitude, the SCR rise time, etc.) obtained by the SCR calculation unit 317 are input to the subtracter unit 320, as shown in FIG. 9.

Furthermore, a detailed configuration and operation of the SKT Mean/Max calculation unit 318 of the feature analysis unit 310 shown in FIG. 9 will be discussed as follows.

Figure 15:
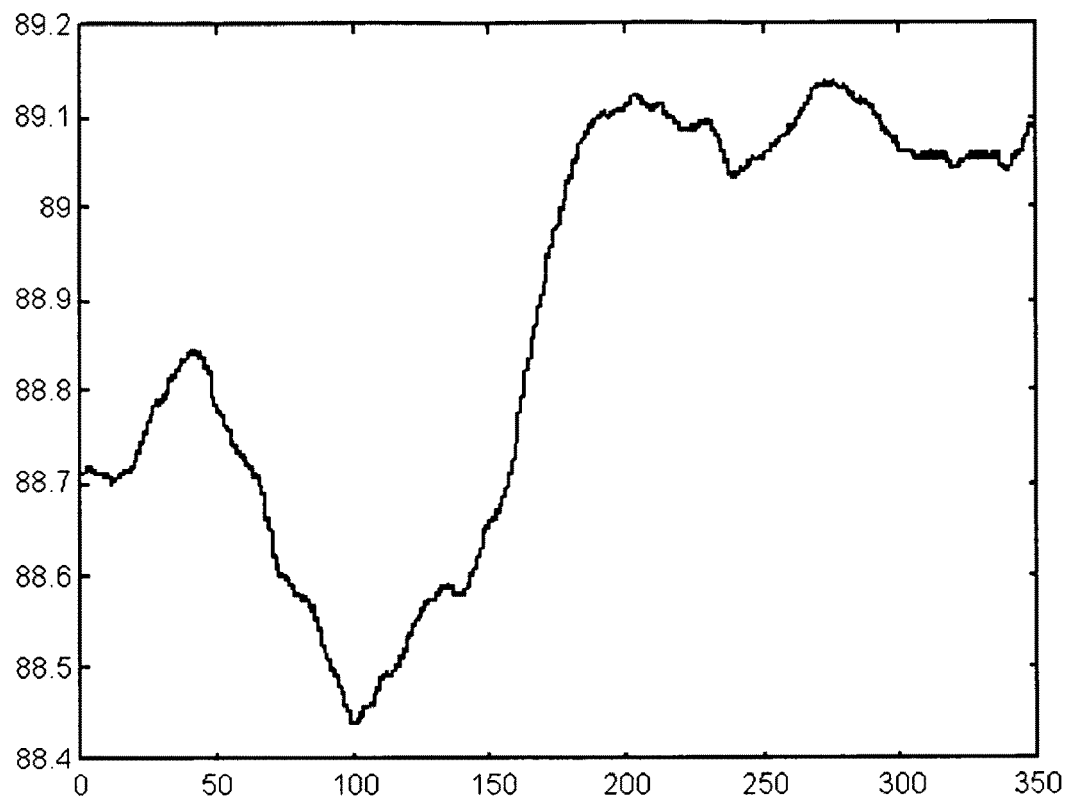
FIG. 15 is a view showing a waveform of an SKT signal used to detect changes in skin temperature.
Figure 16:
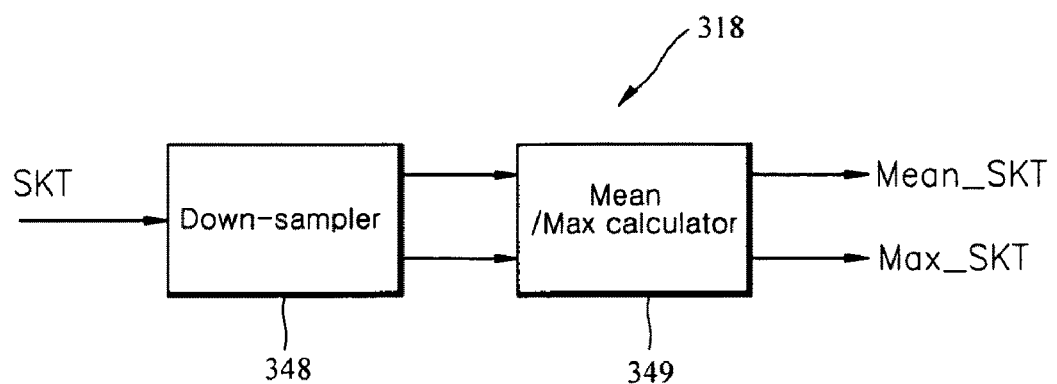
FIG. 16 is a block diagram showing a configuration of an SKT Mean/Max calculation unit shown in FIG. 9.

FIG. 15 is a view showing the waveform of an SKT signal used to detect changes in skin temperature, and FIG. 16 is a block diagram showing the configuration of the SKT Mean/Max calculation unit shown in FIG. 9.

Referring to FIG. 16, the SKT Mean/Max calculation unit 318 comprises a down-sampler 348 and a Mean/Max calculator 349. The SKT Mean/Max calculation unit 318 receives an SKT signal such as shown in FIG. 15 and causes the received signal to be down sampled to about 100 data. Then, a mean Mean_SKT and a maximum value Max_SKT of the down-sampled data are produced as SKT feature data.

As described above, the feature values necessary to recognize the user's emotion are extracted from the plurality of biomedical signals input from the user by means of the heartbeat analysis unit 311, the SCR analysis unit 315 and the SKT Mean/Max calculation unit 318 included in the feature analysis unit 310, and then input sequentially into the subtracter unit 320 and the SVM unit 330 so that the user's emotion can be recognized.

Referring again to FIG. 9, the feature values Feature 1'~Feature 4' for the normal emotional state of the user are stored in the subtracter unit 320 as standard feature values for recognition of the user's emotion. The subtracter unit 320 calculates the difference between a plurality of the feature values Feature 1~Feature 4 input from the heartbeat analysis unit 311, the SCR analysis unit 315 and the SKT Mean/Max calculation unit 318 included in the feature analysis unit 310 and the feature values Feature 1~Feature 4' for the normal emotional state of the user, and then, transmits the difference to the SVM unit 330.

The SVM unit 330 comprises a support vector machine (SVM) classifier 332 for training and classifying the emotional state of the user in response to the difference between the feature values output from the subtracter unit 320, a database 334 for storing the results obtained by the SVM classifier 332, and an emotional determination unit 336 for determining and outputting the stress index and level among the plurality of emotional state values classified by the SVM classifier 332.

If a specific vector for representing a specific emotional state is generally expressed as one probability distribution in a multidimensional space and a probability density functions corresponding to the respective state are already known, a pattern classifier such as the SVM classifier 332 used for classifying the user's emotion may be a statistically optimal classifier according to Bayes' law as explained in "Pattern classification", $2^{nd}$ edition, 2000, published from Wiley by R. O. Duda, P. E. Hart and D. G. Stock.

However, since probability density functions cannot in fact be correctly known, a Parzen window classifier, a multilayer perceptron and the like for implicitly implementing Bayes' law through training with a limited amount of data are frequently used. But, the classifiers have poor generalization characteristics; a very high malfunction rate is obtained when using new data that have not yet been used in the training. Moreover, conventional pattern classifiers have wide a wide distribution for feature vectors and there are large overlapping portions between different state distributions. Thus, it is very likely that the malfunction rate will be increased. In order to solve the above problems, the present invention uses the SVM classifier 332, which is known for showing superior generalization characteristics, as a pattern classifier for use in emotion recognition.

Improvement on linear separation possibilities of the SVM classifier 332 can be obtained by means of multidimensional nonlinear mapping. The SVM classifier 332 is configured using a method for implementing a linear separator having an optimum generalization performance based on the statistical learning theory of Vapnik. A more detailed description is disclosed in the technical paper, "An overview of statistical learning theory", IEEE Transactions on neural network, Vol. 10, No. 5, pp. 988-999, 1999, by V. Vapnik.

Figure 17A:
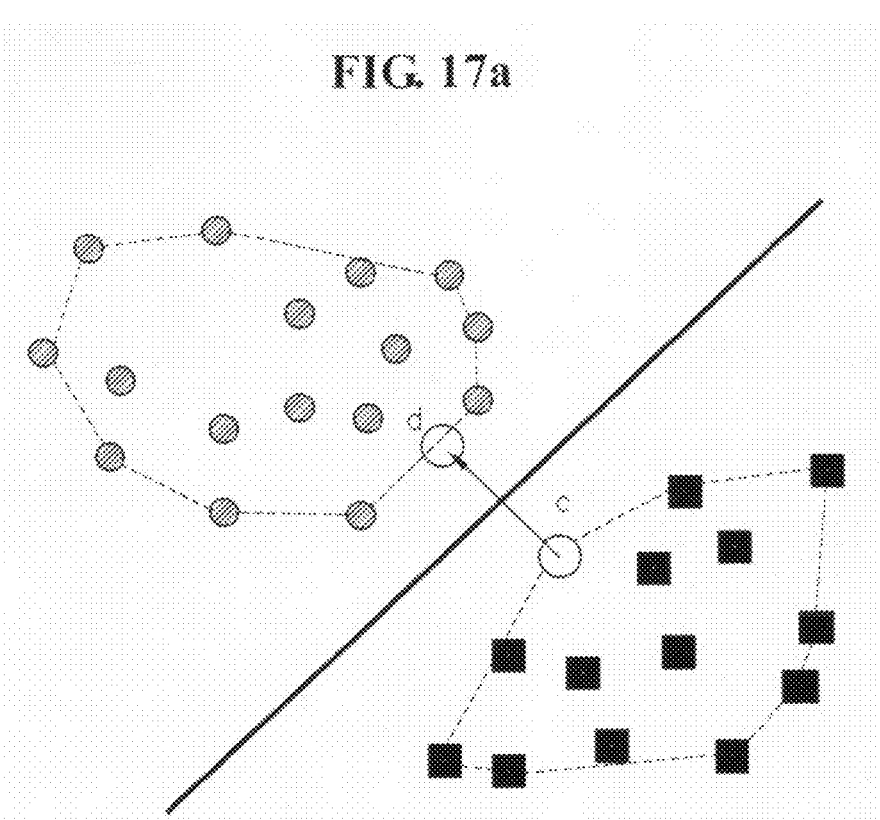
FIGS. 17a and 17b are views showing results of emotion classification by an SVM classifier shown in FIG. 9.
Figure 17B:
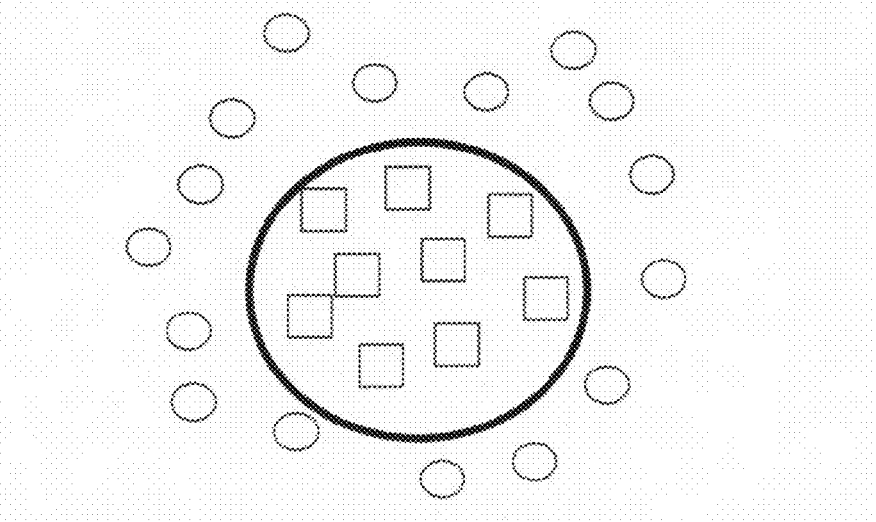

FIGS. 17a and 17b are views showing emotion classification results made by an SVM classifier shown in FIG. 9. The SVM classifier 332 of the present invention linearly projects and analyzes a nonlinearly high order of input space in a feature space, and presents an optimal boundary (i.e., an optimal separating surface) between the feature data (i.e., the user's emotions) as shown in FIGS. 17a and 17b.

Referring again to FIG. 9, the emotion classification results obtained by the SVM classifier 332 are classified according to the respective emotions, and respective emotion intensities are then output in the form of numbers. For example, emotion intensities such as 0.3 (or 30%) corresponding to stress, 0.6 (or 60%) corresponding to sadness, and 0.1 (or 10%) corresponding to anger may be expressed in the form of numbers.

The emotional determination unit 336 receives intensity values for the plurality of emotions from the SVM classifier 332, determines which value corresponds to the stress index and value among the intensity values, and outputs the determined value. At this time, information on what kind of emotions should be recognized in response to the specific input feature values is stored in the database 334. Data updates on the database 334 are performed during the training of the SVM classifier 332. Once the training of the SVM classifier has been completed, data updates on the database 334 are not performed any longer. Therefore, the database 334 is necessary for the developer, but the completely developed emotion recognition system need not be provided with the database 334.

The results of emotion recognition performed by the SVM classifier 332 include delight, sadness, anger, fear, disgust, and surprise. The embodiment of the present invention is configured in such a manner that only the state values of the stress corresponding to an indicator of mental health are output through the emotional determination unit 336 so that only physical fatigue or mental stress can be determined. Of course, other embodiments of the present invention may be configured in such a manner that state values for a variety of emotional states such as delight, sadness, anger, fear, disgust, and surprise are output to determine the emotional state of the user.

Furthermore, the physical condition analysis unit 370 includes a body fat percentage calculation unit 371 and a calorie consumption calculation unit 372. The body fat percentage calculation unit 371 calculates body fat percentage based on the information stored in the memory unit 230, such as the height, weight, age and sex of the user, and the body impedance values detected through the body fat sensor unit 140 and displays the calculated value onto the screen through the display unit 220.

In the meantime, if the people take exercise, the body temperature and heart rate will be raised due to increases in blood flow, and the calories in the body will be consumed. Calorie consumption due to a rise in the body temperature and heart rate should be optimal since optimal calorie consumption causes the body homeostasis and thus the user's health to be kept constant. Accordingly, the calorie consumption calculation unit 372 calculates calorie consumption due to exercise based on the body fat percentage and average heart rate before/after exercising, and displays the calculated value on the screen through the display unit 220. At this time, a value obtained by analyzing the PPG signal measured in the heart rate sensor 110 of the biomedical signal measurement module 100, i.e. the average heart rate analyzed in the heartbeat analysis unit 311, is used as an average heart rate before/after exercise, a value obtained by analyzing the body impedance measured by the body fat sensor unit 140 of the biomedical signal measurement module 100, i.e. the body fat percentage calculated in percent fat by the body calculation unit 371, is used as body fat percentage.

Hereinafter, a health care method using the mobile device according to the present invention will be described in detail with reference to the accompanying drawings.

Figure 18:
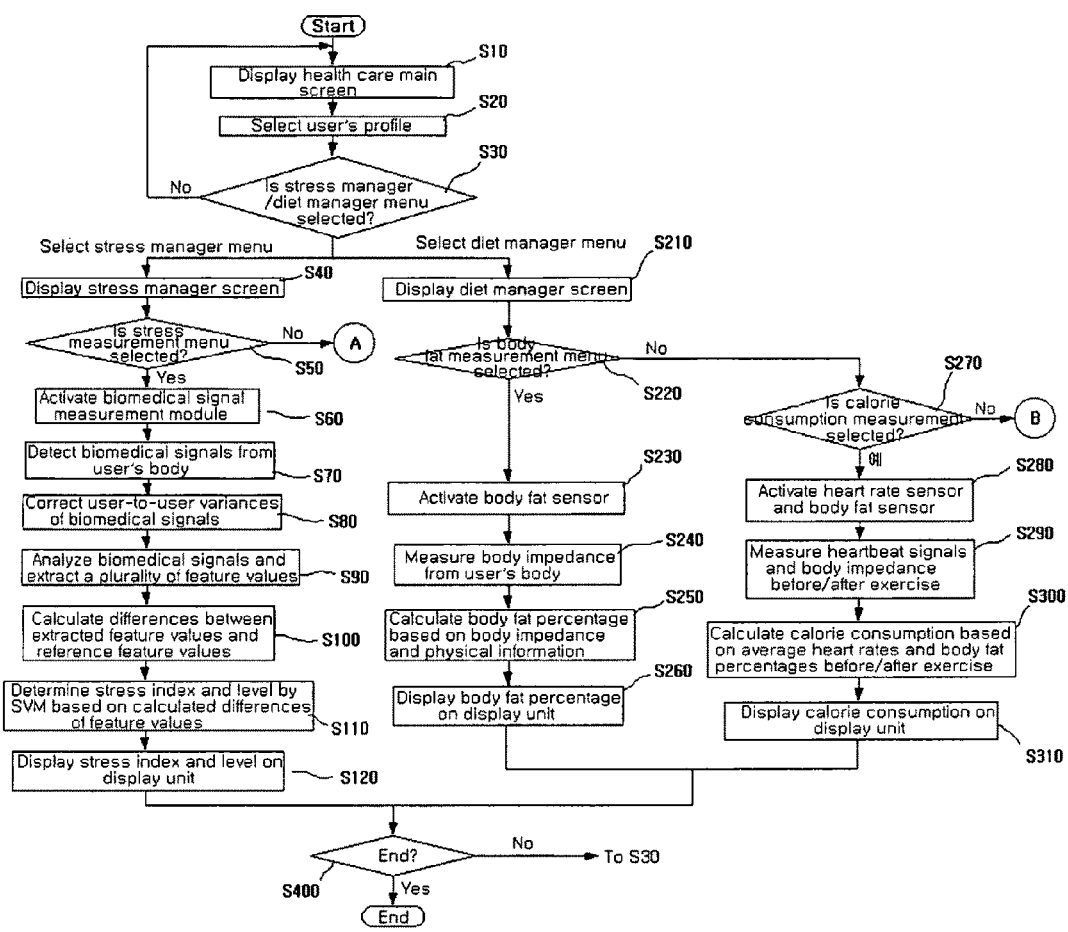
FIG. 18 is a flowchart illustrating a health care method using the mobile device according to the present invention.

FIG. 18 is a flowchart illustrating the health care method using the mobile device according to the present invention.

Figure 22:
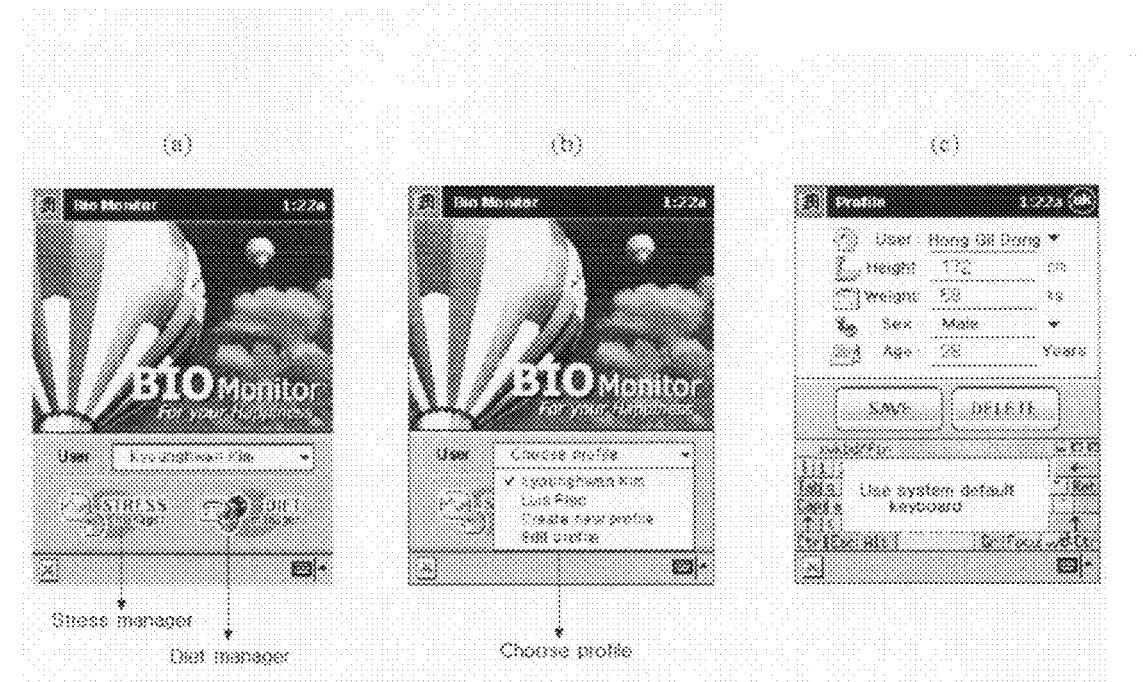
FIG. 22 shows display screens of the mobile device in a case where a health care menu has been selected in the mobile device according to the present invention.

When a user first selects a health care menu on the mobile device 400, a health care main screen is displayed on the display unit 220, as shown in FIG. 22 (S10). In this state, the user chooses his/her own profile, as shown in FIG. 22b (S20).

At this time, if there is no user's profile, the user can also directly input data such as user's name, height, weight, sex and age to create a user's profile, as shown in FIG. 22c.

Then, if the user selects a stress manager menu, a stress manager main screen is displayed on the display unit, as shown in FIG. 23 (S30 and S40). In this state, if the user selects a stress measurement menu, a guide message for biomedical signal measurement is displayed on the display unit and the biomedical signal measurement module 100 is simultaneously activated, as shown in FIG. 23b (S50 and S60).

Figure 23A:
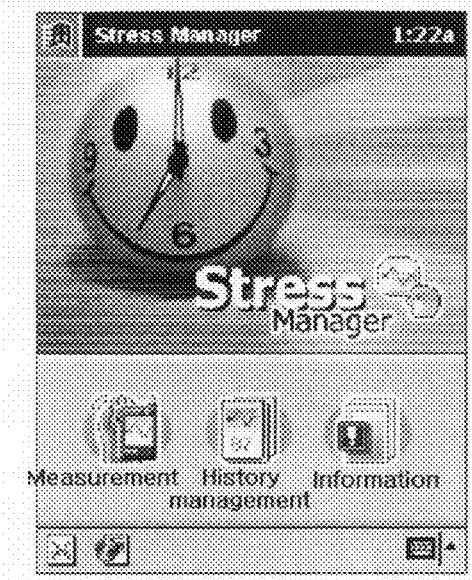
FIGS. 23a to 23d show display screens of the mobile device in a case where a stress manager menu has been selected in the mobile device according to present invention.
Figure 23B:
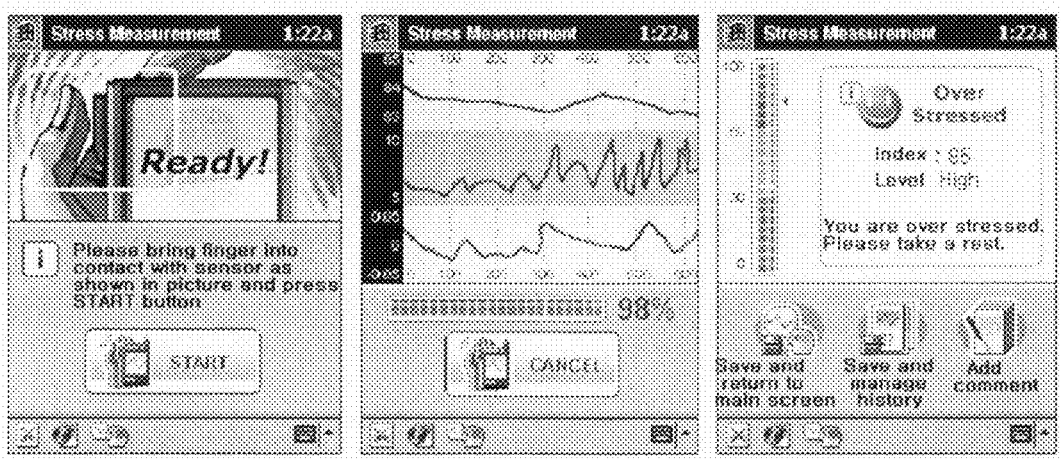

Subsequently, when the user presses the start button according to the guide message while holding the mobile device 400, a plurality of biomedical signals such as heartbeat, skin temperature and skin resistance are detected from a user's body through the biomedical signal measurement module 100, and the detected biomedical signals are displayed on the display unit so that the user can confirm the results, as shown in FIG. 23b (S70). A status window for indicating a ratio of completion of biomedical signal measurement may be displayed on the display unit.

Figure 19:
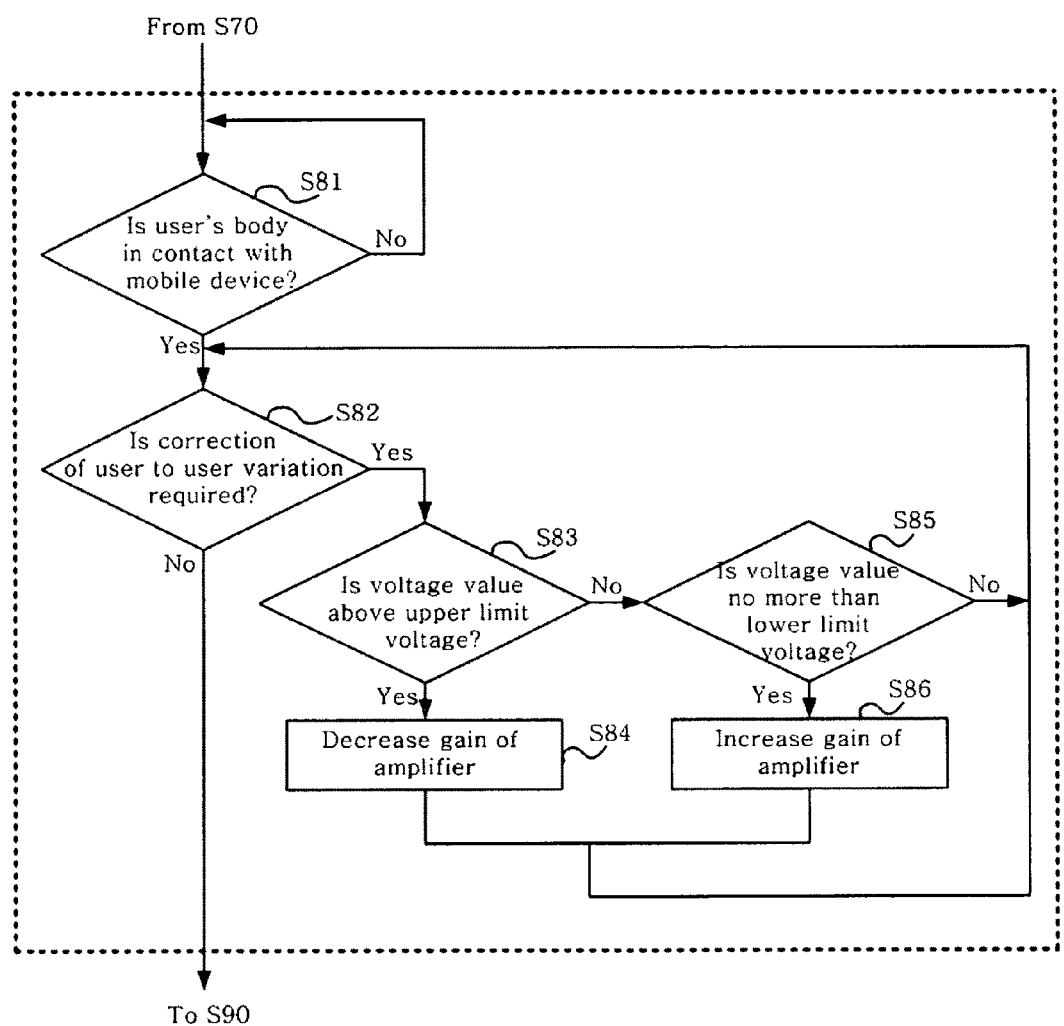
FIG. 19 is a flowchart specifically illustrating a step of correcting the user-to-user variation of biomedical signals shown in FIG. 18.

In the meantime, since the user-to-user variation of the biomedical signals measured through the biomedical signal measurement module 100 large according to response sensitivity and measurement environment, there may be cases where the emotional state of the user cannot be correctly determined due to the variation. To this end, the user-to-user variation is corrected in an initial measurement stage (S80). The step of correcting the user-to-user variance of the biomedical signals S80 will be described hereinafter in greater detail with reference to FIG. 19.

As described above with reference to FIGS. 4 and 5, since the user-to-user variation of skin resistance values of the biomedical signals measured through the biomedical signal measurement module 100 is large, the following description will be focused on skin resistance values.

First, it is determined whether user's body is in contact with the biomedical signal measurement module 100, by checking whether a voltage value $V_0$ input from the skin resistance sensor 130 of the biomedical signal measurement module 100 is larger than a threshold voltage value $V_{th}$ (S81). Here, the threshold voltage value $V_{th}$ is a minimum voltage value, which indicates that the user's body is in contact with the biomedical signal measurement module 100. It is preferred that the threshold voltage value $V_{th}$ be stored beforehand in the memory unit 230.

If it is determined that the user's body is in contact with the biomedical signal measurement module 100, i.e. $V_0 \geq V_{th}$, it is checked whether the input voltage value $V_0$ is equal to or larger than a lower limit voltage $V_{cutoff\_min}$ but equal to or smaller than a upper limit voltage $V_{cutoff\_max}$, i.e. $V_{cutoff\_min} \leq V_0 \leq V_{cutoff\_max}$. Based on the check result, it is determined whether correction of the user-to-user variation of skin resistance values is required (S82).

If it is determined that variation correction is required, i.e. $V_{cutoff\_min} \leq V_0 \leq V_{cutoff\_max}$ is not established, it is checked whether the input voltage value $V_0$ is above the upper limit voltage $V_{cutoff\_max}$ (S83). If it is above the upper limit voltage $V_{cutoff\_max}$, the resistance value R of the variable resistor is reduced to decrease the gain of the amplifier 133 (S84).

If the input voltage value $V_0$ is equal to or less than the upper limit voltage $V_{cutoff\_max}$, it is checked whether the input voltage value $V_0$ is smaller than the lower limit voltage $V_{cutoff\_min}$ (S85). If it is smaller than the lower limit voltage $V_{cutoff\_min}$, the resistance value R of the variable resistor is increased to increase the gain of the amplifier 133 (S86).

The voltage value $V_0$ input from the skin resistance sensor 130 through the step of correcting the user-to-user variation can be maintained to be equal to or larger than the lower limit voltage but equal to or smaller than the upper limit voltage. Accordingly, correct biomedical signals on which a change in the emotional state of the user is properly reflected can be detected by correcting the user-to-user variation according to response sensitivity and measurement environment.

After the user-to-user variation correction of the biomedical signals is completed, the health care module 300 analyzes the biomedical signals such as the PPG signals, EDA signals, and SKT signals detected from the user's body and extracts a plurality of feature values used for determining the emotional state of the user (S90).

As for the feature values extracted in step S90, there are a spectrum of heartbeat signals extracted from PPG signals, a mean value and standard deviation value of heartbeat signals, SCR-related parameters detected from EDA signals, mean and maximum values extracted from SKT signals, and the like.

Then, differences between the plurality of extracted feature values and feature values on which the emotional state is determined are calculated (S100). Here, the feature values on which the emotional state is determined are feature values indicating a normal emotional state in which the user is not biased toward a specific emotion. It is preferred that the feature values on which the emotional state is determined be stored in advance.

When the differences between the feature values are obtained, the emotional state of the user is determined based on the SVM classification according to the differences. The emotional state of the user is first classified by respective emotions and stress-related values are then selected from the respective emotions so as to calculate a stress index and level (S110).

The calculated stress index and level are displayed on the display unit as shown in FIG. 23b so that the user can check them (S120). In this state, the user may add a comment on a situation causing the stress or check the stress status on a daily, weekly or monthly basis.

Figure 20:
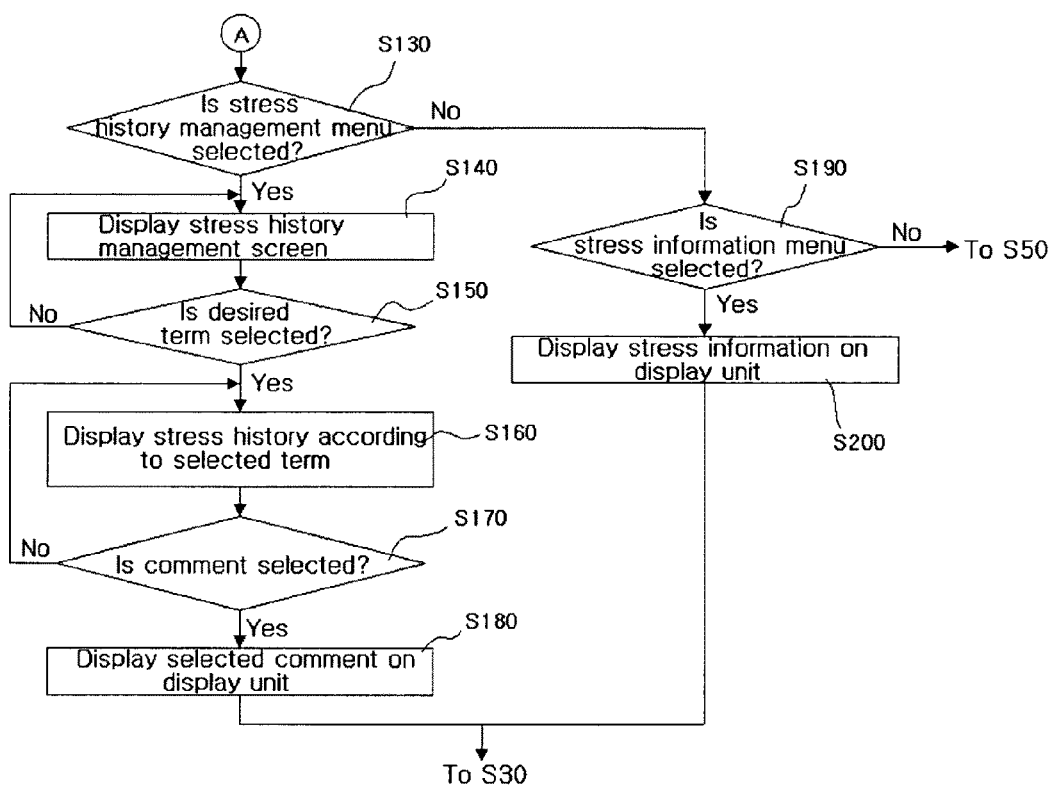
FIG. 20 is a flowchart illustrating a step of managing stress history and providing stress information shown in FIG. 18.

Meanwhile, a case where the user selects a stress history management menu or stress information menu on the stress manager main screen of FIG. 23a will be described with reference to FIG. 20.

Figure 23C:
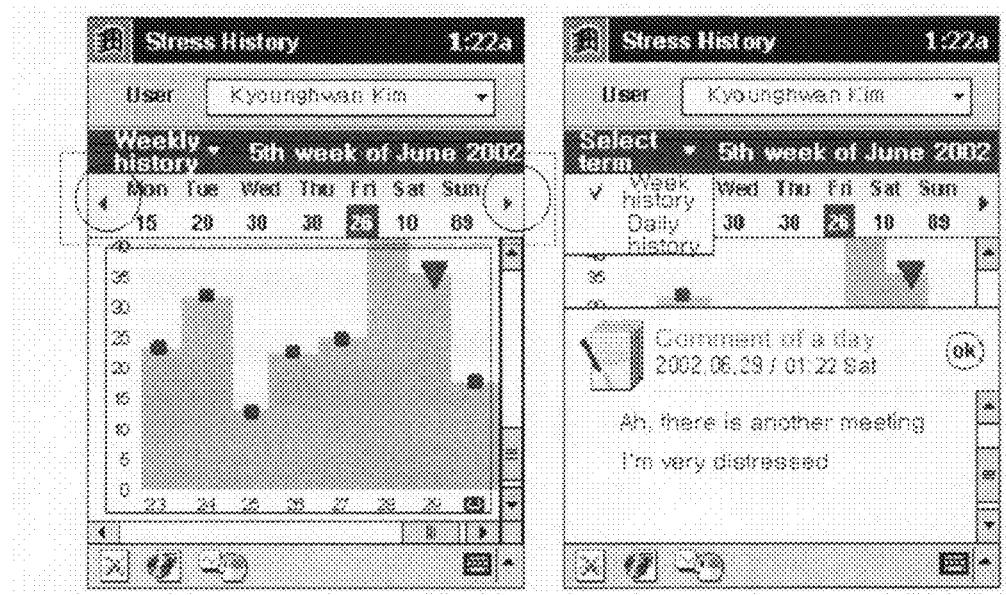

If the user selects the stress history management menu on the stress manager main screen, the stress history management screen is displayed as shown in FIG. 23c (S130 and S140). In this state, if the user selects a desired term, a stress history is displayed on the display unit according to the selected term (S150 and S160). In the state where the stress history is displayed on the display unit, if the user selects a comment on a specific date, the selected comment is displayed on the display unit (S170 and S180).

Figure 23D:
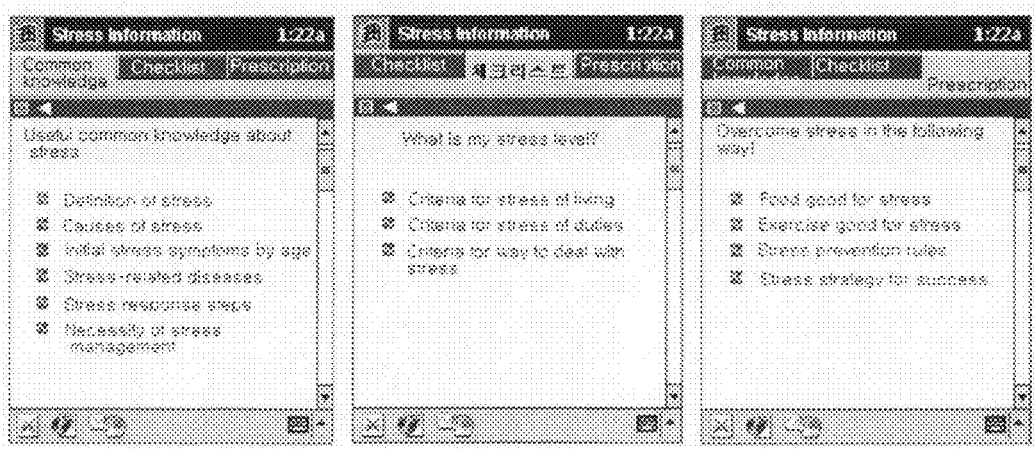

On the other hand, if the user selects the stress information menu on the stress manager main screen, information on stress is displayed on the display unit as shown in FIG. 23d (S190 and S200).

The emotional state determination method of the present invention observes and analyzes the biomedical signals for a short period of time of about 50 seconds by using the ARMA-sel algorithm instead of the conventional periodogram method that is performed for signals over a long period of time from a few minutes to 24 hours. Further, upon determination of the user's emotional state, the determination is performed by using the SVM classifier that exhibits high generalization characteristics. Therefore, the biomedical signals of the user can be monitored for a short period of time and the emotional state of the user can be correctly recognized.

Referring again to FIG. 18, if the user selects the diet manager menu on the health care main screen, a diet manager main screen is displayed on the display unit as shown in FIG. 24 (S210).

Figure 24A:
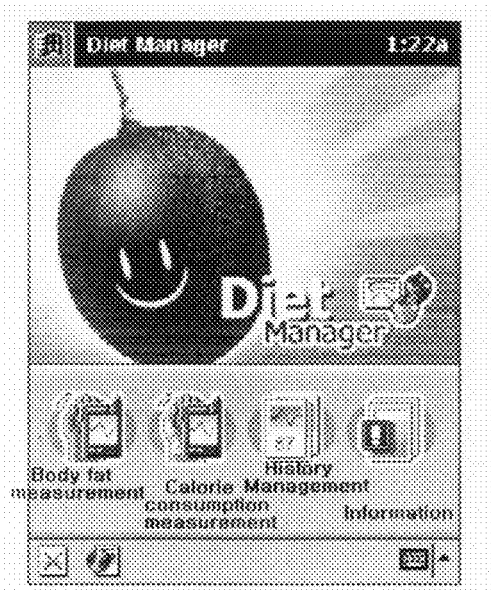
FIGS. 24a to 24e show display screens of the mobile device in a case where a diet manager menu has been selected in the mobile device according to the present invention.
Figure 24B:
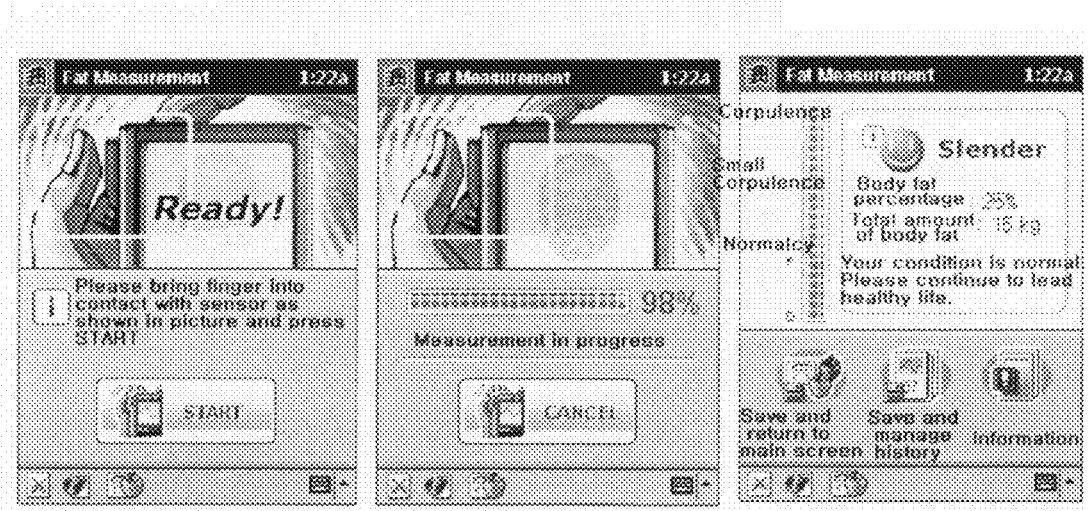

If the user selects the body fat measurement menu in this state, the body fat sensor 140 of the biomedical signal measurement module 100 is activated while a guide message for body fat measurement is displayed on the display unit as shown in FIG. 24b (S220 and S230).

When the user presses the measurement start button according to the guide message while holding the mobile device 400, a body impedance value is measured from the user's body through the body fat sensor 140, and the measured body impedance value is displayed on the display unit as shown in FIG. 24b so that the user can confirm the measurement result (S240). At this time, the status window for indicating the ratio of completion of biomedical signal measurement may also be displayed on the display unit.

Then, body fat percentage BodyFat % of the user's body is calculated based on the measured impedance value and the user's height, weight, age and sex stored in the memory unit 230, and the calculated body fat percentage is displayed on the display unit as shown in FIG. 24b (S250 and S260). At this time, the body fat percentage BodyFat % is expressed as the following formula 1 that is a function of the measured body impedance value R and the user's height, weight, age and sex.

$$FFM = a*Height^2/R + b*Weight - c*Age + d*Sex + e$$

$$BodyFat = 100 * \frac{Weight - FFM}{Weight} \quad (1)$$

The FFM in Formula 1 means Fat Free Mass that is a weight excluding body fat. Values of a, b, c and d are determined based on a multiple regression model selected according to the user's body impedance value R, and the information on the height, weight, age and sex that have been input. The FFM is calculated according to the determined values of a, b, c and d.

In the present embodiment, the body fat percentage has been calculated with the parameters of height, weight, age and sex having relatively great influences on the FFM among user's physical information. However, other parameters may be used for the calculation of the body fat percentage.

Figure 24C:
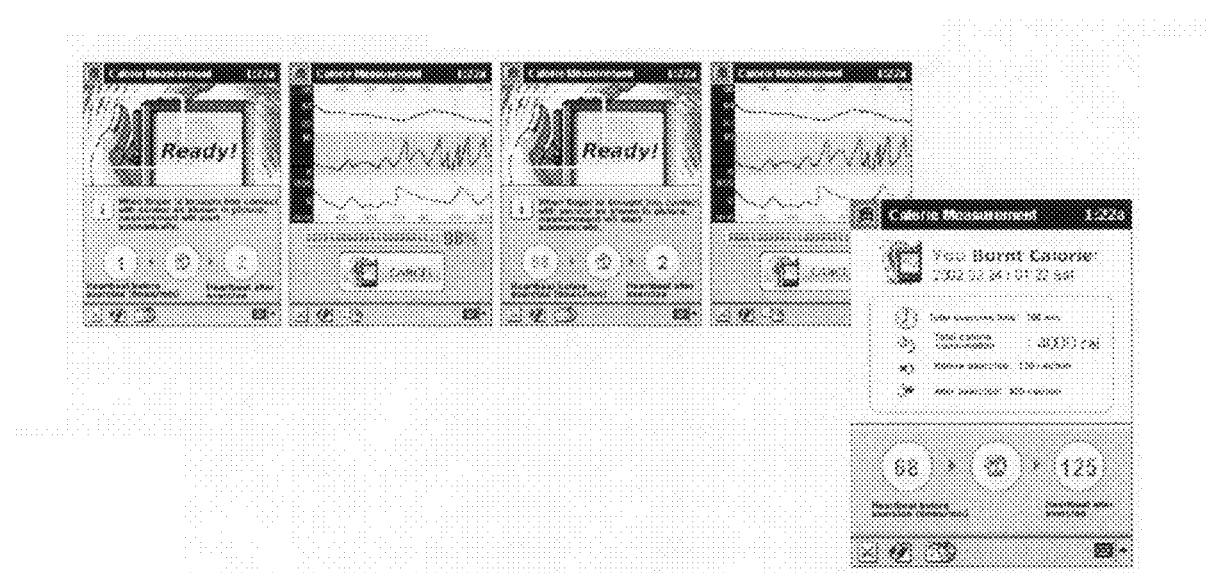

In the meantime, if the user selects the calorie consumption measurement menu on the diet manager main screen, the heart rate sensor 110 and the body fat sensor 140 of the biomedical signal measurement module 100 are activated while a guide message for calorie consumption measurement is displayed on the display unit as shown in FIG. 24c (S270 and S280).

Then, when the user presses the measurement start button according to the guide message while holding the mobile device 400, the heart rate sensor 110 measures PPG signals before exercise from the user's body while the body fat sensor 140 measures the body impedance from the user's body. After exercise is completed, the heart rate sensor 110 measures PPG signals from the user's body once more (S290). At this time, the measured PPG signals are displayed on the display unit as shown in FIG. 24c so that the user can check the measurement results, and the status window for indicating the ratio of completion of the biomedical signal measurement may also be displayed.

Then, the heartbeat signals and body impedance values before/after the exercise are analyzed to calculate average heart rates and body fat percentages before/after the exercise. Calorie consumption due to exercise is calculated based on the calculated average heart rates and body fat percentages before/after exercise, exercise time, and the user's height, weight, age and sex. The calculated calorie consumption is displayed on the display unit as shown in FIG. 24c (S300 and S310).

The calculation of the calorie consumption will be described in greater detail. The calorie consumption due to can vary according to a user's basal metabolic rate. Since the basal metabolic rate is determined depending on the user's weight and body fat percentage, it is necessary to accurately measure the user's basal metabolic rate in order to calculate correct calorie consumption.

However, in order to accurately measure the user's basal metabolic rate, expensive equipment is required and the user should rest for a long time while wearing a facial mask and a mouthpiece. For this reason, a method of calculating calorie consumption by multiplying standard values of basal metabolic rates predetermined on the basis of sex and age by user's weight has been generally used.

However, since the standard values of the basal metabolic rates are calculated based on persons with standard physical figures, there may be great differences between the standard values and actual basal metabolic rates of users according to corpulence, slenderness, sex and age of each user. Therefore, the calorie consumption due to exercise cannot be correctly checked.

In order to solve this problem, according to the present invention, the body fat percentage is obtained based on the body impedance measured by the body fat sensor 140 and the user's basal metabolic rate is then calculated based on the acquired body fat percentage. Since such a calorie consumption calculation method is disclosed in detail in Japanese Patent Laid-Open Publication No. 1996-52119, a detailed description thereof will be omitted.

Figure 21:
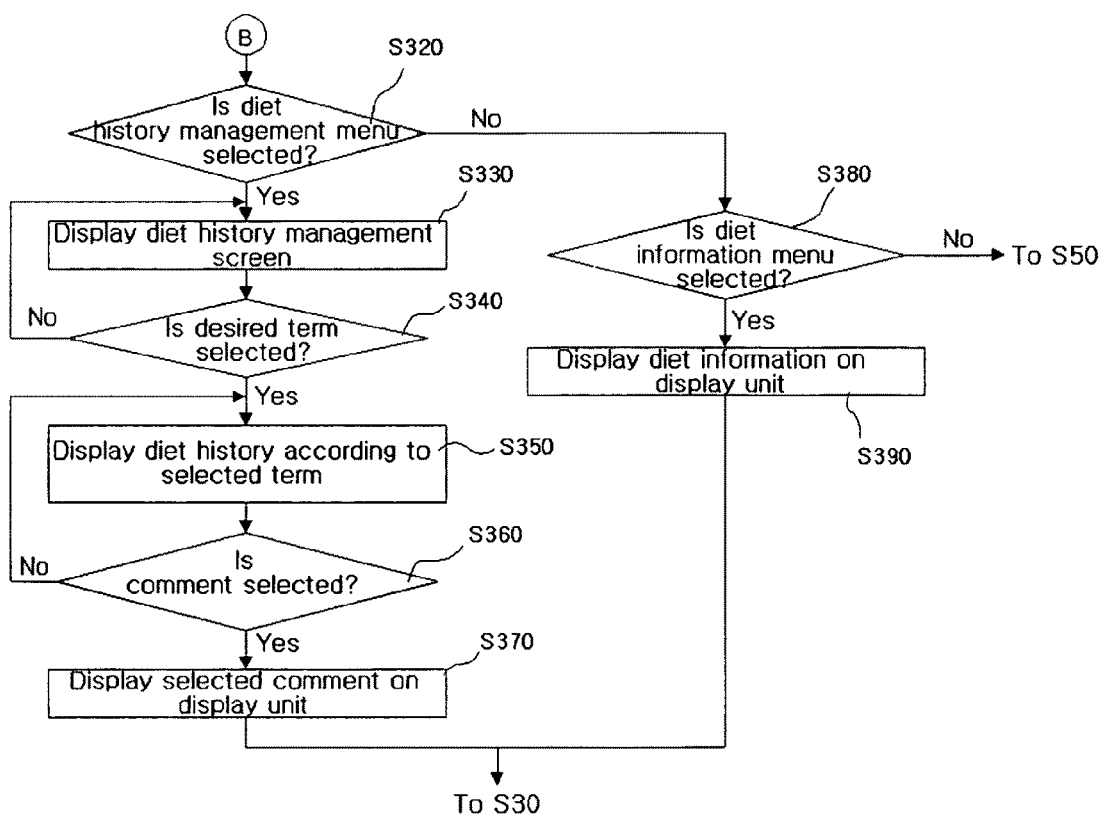
FIG. 21 is a flowchart illustrating a step of managing diet history and providing diet information shown in FIG. 18.

Next, a case where the user selects the diet history management menu or diet information menu on the diet manager main screen of FIG. 24*a* will be described with reference to FIG. 21.

Figure 24D:
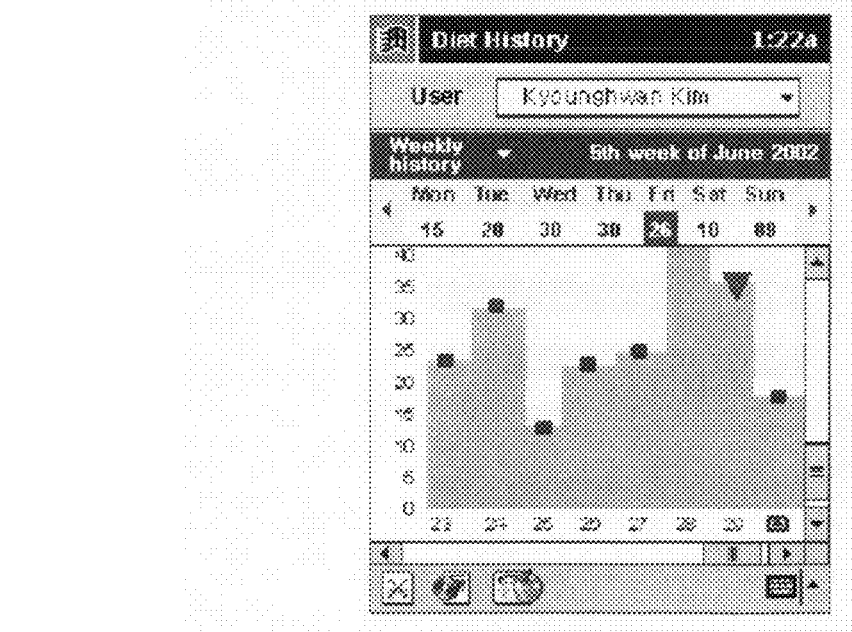

If the user selects the diet history management menu on the diet manager main screen, diet history management screen, a diet history management screen is displayed as shown in FIG. 24*d* (S320~S330). If the user selects a desired term in this state, a diet history is displayed on the display unit according to the selected term (S340 and S350). In a state where the diet history is displayed on the display unit, if the user selects a comment on a specific date, the selected comment is displayed on the display unit (S360 and S370).

Figure 24E:
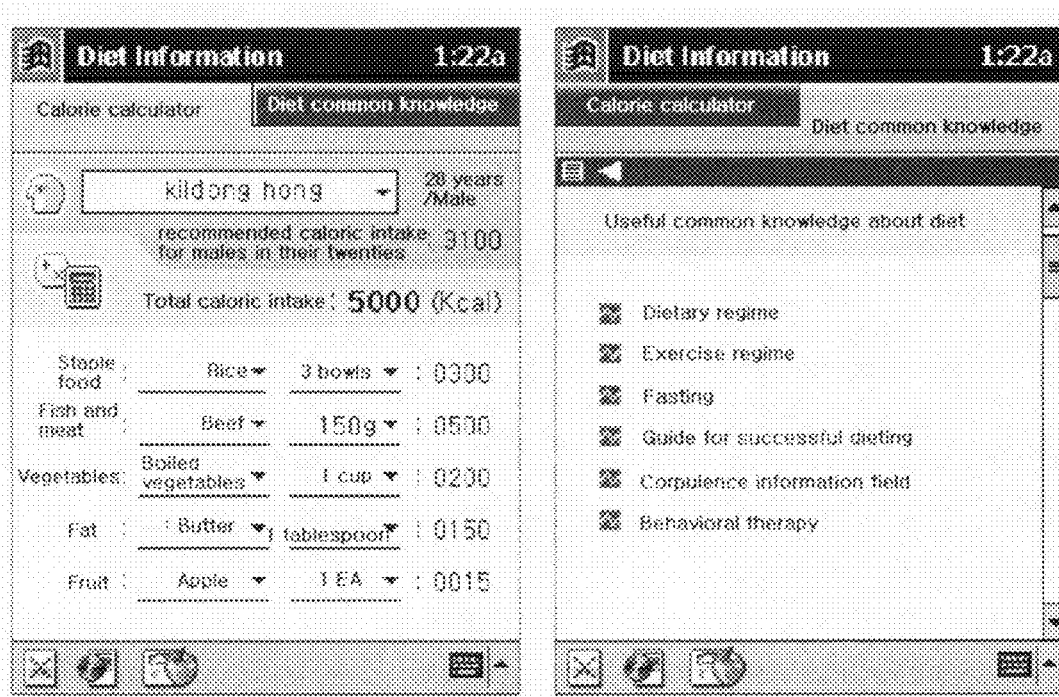

Meanwhile, if the user selects the diet information menu on the diet manager main screen, information on a diet is displayed on the display unit as shown in FIG. 24*e* (S380 and S390).

As described above, the stress level, the body fat percentage of the user's body and the calorie consumption due to exercise can be measured at any time if necessary by using the mobile device according to the present invention.

According to the present invention, the user can conveniently check his/her own emotional state and physical condition at any time by using the mobile device. Therefore, there is an advantage in that modern people who lack time to care for their health can more easily manage their own health condition.

Further, according to the present invention, there is an advantage in that the users can simply check their own emotional state and physical condition through natural operations for using the mobile device.

Moreover, according to present invention, service differentiation can be promoted by adding functions, which can greatly interest users, to the mobile device. Therefore, there is an advantage in that a manufacturer of the mobile device can obtain increased benefits by manufacturing terminals capable of cooperating with a variety of physical condition measurement devices.

Although the present invention has been described in connection with the preferred embodiment illustrated in the drawings, this is merely illustrative. It will be understood by those skilled in the art that various modifications, changes and equivalents can be made thereto. In particular, although the present invention has been described by way of example in connection with the case where stress is selected among a variety of emotions and the level of stress is checked, the health care method of the present invention is not limited thereto but can allow the checking of a variety of emotions based on a variety of biomedical signals measured by the biomedical signal measurement module. Therefore, the true technical scope of the present invention should be defined by the scope of the appended claims.

What is claimed is:

1. A mobile device with an input unit, a display unit, a memory unit and a central control unit, the mobile device comprising:
   a biomedical signal measurement module that detects biomedical signals from a user's body, and classifies the detected biomedical signals by respective signals outputting the classified signals; and
   a processor that:
   analyzes an emotional state and physical condition of the user based on the classified signals input from the biomedical signal measurement module and physical information of the user,
   extracts feature values of the classified biomedical signals input from the biomedical signal measurement module,
   obtains differences between the extracted feature values and predetermined feature values,
   classifies the user's emotional state by respective emotions in accordance with the differences of the feature values,
   analyzes the user's physical condition based on the classified biomedical signals input from the biomedical signal measurement module and the user's physical information, and
   selects values related to a specific emotion among values of the plurality of classified emotions and calculates and outputs an index and a level for the specific emotion.

2. The mobile device are claimed in claim 1, wherein the biomedical signal measurement module comprises:
   a sensor unit for detecting one or more biomedical signals from the user's body; and
   a sensor control unit for controlling the sensor unit, classifying the biomedical signals input from the sensor unit by the respective biomedical signals and outputting the classified biomedical signals.

3. The mobile device as claimed in claim 2, wherein the sensor unit comprises a hear rate sensor for detecting heartbeat-related biomedical signals.

4. The mobile device as claimed in claim 3, wherein the biomedical signals of heartbeat are photoelectric pulse plethysmograph (PPG) signals.

5. The mobile device as claimed in claim 2, wherein the sensor unit comprises a skin temperature sensor for detecting skin temperature-related biomedical signals.

6. The mobile device as claimed in claim 2, wherein the biomedical signals of skin temperature are skin temperature (SKT) signals.

7. The mobile device as claimed in claim 2, wherein the sensor unit comprises a skin resistance sensor for detecting skin resistance-related biomedical signals.

8. The mobile device as claimed in claim 7, wherein the biomedical signals of skin resistance are electrodermal activity (EDA) signals.

9. The mobile device as claimed in claim 2, wherein the sensor unit comprises a body fat sensor for measuring body impedance required for calculation of a body fat percentage.

10. The mobile device as claimed in claim 2, wherein the sensor unit comprises at least one of a heart rate sensor, skin temperature sensor, skin resistance sensor and body fat sensor, and the sensor unit further comprises a filter for filtering the detected biomedical signals and an amplifier for amplifying the filtered biomedical signals.

11. The mobile device as claimed in claim 2, wherein the sensor unit comprises at least one of heart rate sensor, skin temperature sensor, skin resistance sensor and body fat sensor and wherein the sensor unit is installed at a position on the mobile device with which user's hand comes into contact when the user holds the mobile device.

12. The mobile device as claimed in claim 2, wherein the sensor control unit corrects user-to-user variation of the biomedical signals that are output from the sensor unit.

13. The mobile device as claimed in claim 1, wherein the biomedical signal measurement module is constructed to be detachably coupled to the mobile device.

14. The mobile device as claimed in claim 13, wherein the biomedical signal measurement module is constructed in the form of a case capable of accommodating the mobile device therein.

15. The mobile device as claimed in claim 1, wherein the processor
  receives photoelectric pulse plethysmograph (PPG) signals to detect heartbeat signals and extracts feature values related to the heartbeat signals;
  receives electrodermal activity (EDA) signals and extracts feature values related to a skin conductive response; and
  receives skin temperature (SKT) signals and extracts feature values related to skin temperature.

16. The mobile device as claimed in claim 15, wherein the processor further
  receives the PPG signals to detect the heartbeat signals and converts the detected heartbeat signals into time series signals of heart rate variability;
  analyzes a spectrum of the heartbeat signals in response to the time series signals of the heart rate variability; and
  calculates a mean value and standard deviation value of the heartbeat signals in response to the time series signals of the heart rate variability.

17. The mobile device as claimed in claim 16, wherein the processor further
  extracts signals falling within a specific band of the PPG signals;
  removes noise existing in the filtering results of the band pass filter;
  calculates a difference between the filtering results of both the band pass filter and the median filter by adding a reciprocal number of the filtering result of the median filter to the filtering result of the band pass filter;
  extracts the heartbeat signals from output signals of the adder; and
  performs zero clipping for the heartbeat signals.

18. The mobile device as claimed in claim 1, wherein the processor uses feature values of a normal emotional state for the user as the predetermined feature values on which the user's emotional state is determined.

19. The mobile device as claimed in claim 1, wherein the processor further
  classifies the user's emotional state into a plurality of emotions by analyzing the differences of the features values obtained from the processor.

20. The mobile device as claimed in claim 19, wherein the processor further stores a plurality of pieces of emotion data for training the SVM classifier, and trained results of the SVM classifier based on the emotion data.

21. The mobile device as claimed in claim 1, wherein the processor
  calculates body fat percentage based on a body impedance value detected by the biomedical signal measurement module and user's height, weight, age and sex; and
  a calorie consumption calculator calculating calorie consumption due to exercise based on average heart rates and body fat percentages before/after exercise detected by the biomedical signal measurement module.

22. A health care method using a mobile device, comprising the:
  detecting biomedical signals from a user's body;
  classifying the detected biomedical signals by respective signals;
  analyzing an emotional state of the user by extracting a plurality of feature values from the classified biomedical signals, calculating differences between the extracted feature values and predetermined feature values, and classifying the user's emotional state by respective emotions based on support vector machine (SVM) classification in accordance with the calculated differences of the feature values; and
  analyzing a physical condition of the user based on the classified signals and user's physical information,
  the analyzing the emotional state comprising selecting values related to a specific emotion among values of the plurality of emotions classified by the SVM classifier and calculating and outputting an index and a level for the specific emotion.

23. The method as claimed in claim 22, further comprising:
  selecting, by the user, a health care menu on a mobile device with a biomedical signal measurement module; and
  if the user selects emotional state measurement, activating the biomedical signal measurement module to detect the biomedical signal in the mobile device.

24. The method as claimed in claim 23, wherein the biomedical signal measurement module is configured to be detachably coupled to the mobile device.

25. The method as claimed in claim 24, wherein the biomedical signal measurement module is constructed in the form of a case capable of accommodating the mobile device therein.

26. The method as claimed in claim 23, further comprising the steps of, if the user selects body fat measurement,
  activating a body fat sensor in the biomedical signal measurement module mounted to the mobile device;
  measuring body impedance from the user's body by the body fat sensor; and
  calculating a body fat percentage of the user's body based on the measured impedance and user's physical information and displaying the calculated the body fat percentage on the display unit.

27. The method as claimed in claim 23, further comprising the steps of, if the user selects calorie consumption measurement,
  activating a heart rate sensor and a body fat sensor in the biomedical signal measurement module;
  measuring heartbeat signals and body impedance before/after exercise from the user's body by the heart rate sensor and the body fat sensor; and
  analyzing the heartbeat signals and the body impedance before/after exercise to calculate average heart rates and body fat percentages before/after exercise, calculating calorie consumption due to exercise based on the calculated average heart rates and body fat percentages before/after exercise, exercise time, and user's physical information, and displaying the calculated calorie consumption on the display unit.

28. The method as claimed in claim 23, further comprising the step of, if the user selects history management, displaying measurement results according to respective desired terms on the display unit.

29. The method as claimed in claim 22, further comprising:
classifying the user's emotional state into a plurality of emotions by analyzing the differences of the features values; and
selecting values related to an emotion selected among the classified emotions, calculating an emotional state index and level for the selected emotion, and displaying the calculated emotional state index and level on a display unit of the mobile device.

30. The method as claimed in claim 22, wherein the biomedical signals detected from the user's body include biomedical signals of heartbeat.

31. The method as claimed in claim 30, wherein the biomedical signals of heartbeat are photoelectric pulse plethysmograph (PPG) signals.

32. The method as claimed in claim 22, wherein the biomedical signals detected from the user's body include skin temperature-related biomedical signals.

33. The method as claimed in claim 32, wherein the biomedical signals of skin temperature are skin temperature (SKT) signals.

34. The method as claimed in claim 22, wherein the biomedical signals detected from the user's body include skin resistance-related biomedical signals.

35. The method as claimed in claim 34, wherein the biomedical signals of skin resistance are electrodermal activity (EDA) signals.

36. The method as claimed in claim 22, wherein the biomedical signals detected from the user's body are filtered by a filter and then amplified by an amplifier.

37. The method as claimed in claim 22, further comprising the step of correcting user-to-user variation of the biomedical signals detected from the user's body, the correcting the user-to-user variation comprising:
determining whether the user's body is in contact with the biomedical signal measurement module;
if it is determined that the user's body is in contact with the biomedical signal measurement module, determining whether the correction of the user-to-user variances of the detected biomedical signals is required;
if it is determined that the correction of the user-to-user variances of the detected biomedical signals is required, checking whether values of the detected biomedical signals are above a maximum limit level and decreasing a gain of an amplifier if the values of the detected biomedical signals are above the maximum limit level; and
if the values of the detected biomedical signals are equal to or less than the maximum limit level, checking whether the values of the detected biomedical signals are equal to or less than a minimum limit level and increasing the gain of the amplifier if the values of the detected biomedical signals are equal to or less than the minimum limit level.

38. The method as claimed in claim 22, wherein the step of analyzing the biomedical signals and extracting the plurality of feature values to be used for determining the user's emotional state comprises the steps of:
receiving photoelectric pulse plethysmograph (PPG) signals to detect heartbeat signals and extracting feature values related to the heartbeat signals;
receiving electrodermal activity (EDA) signals and extracting features values related to a skin conductive response; and
receiving skin temperature (SKT) signals and extracting feature values related to skin temperature.

39. The method as claimed in claim 22, wherein the predetermined feature values on which the user's emotional state is determined are feature values for a normal emotional state of the user.

40. The method as claimed in claim 22, wherein the step of classifying the user's emotional state by the respective emotions uses an SVM classifier that classifies the user's emotional state into a plurality of emotions based on a statistical learning theory.

* * * * *

UNITED STATES PATENT AND TRADEMARK OFFICE
CERTIFICATE OF CORRECTION

PATENT NO. : 8,109,874 B2
APPLICATION NO. : 10/681137
DATED : February 7, 2012
INVENTOR(S) : Donggeon Kong et al.

It is certified that error appears in the above-identified patent and that said Letters Patent is hereby corrected as shown below:

First Page Column 1 Item (75) Inventors (Third Inventor), delete "Kyungki-do" and insert -- Kyunggi-do --, therefor.

First Page Column 1 Item (75) Inventors (Fourth Inventor), delete "Kyungki-do" and insert -- Kyunggi-do --, therefor.

Column 22, Line 5-6, In Claim 22, delete "comprising the:" and insert -- comprising: --, therefor.

Column 22, Line 49, In Claim 26, delete "the body" and insert -- body --, therefor.

Signed and Sealed this
Twenty-ninth Day of May, 2012

David J. Kappos
*Director of the United States Patent and Trademark Office*